Figure 1:
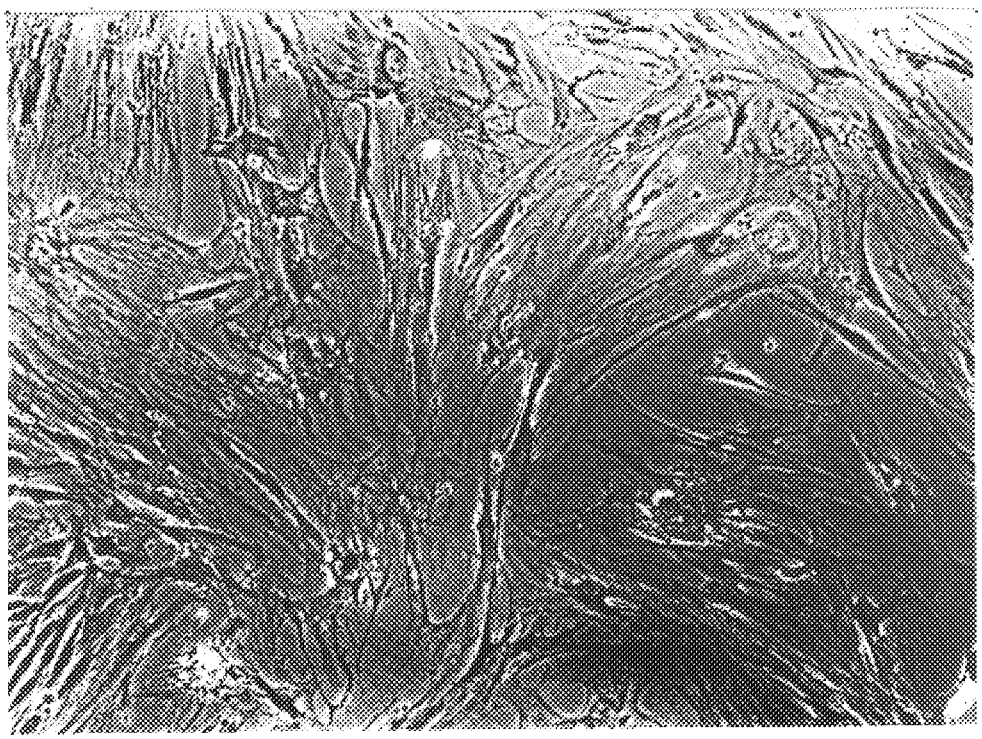

United States Patent [19]
Caplan et al.

[11] Patent Number: 5,811,094
[45] Date of Patent: *Sep. 22, 1998

[54] CONNECTIVE TISSUE REGENERATION USING HUMAN MESENCHYMAL STEM CELL PREPARATIONS

[75] Inventors: Arnold I. Caplan; Stephen E. Haynesworth, both of Cleveland Heights, Ohio

[73] Assignee: Osiris Therapeutics, Inc., Baltimore, Md.

[ * ] Notice: The term of this patent shall not extend beyond the expiration date of Pat. No. 5,486,359.

[21] Appl. No.: 420,297

[22] Filed: Apr. 11, 1995

Related U.S. Application Data

[63] Continuation-in-part of Ser. No. 193,262, Feb. 8, 1994, Pat. No. 5,486,359, which is a continuation-in-part of Ser. No. 34,272, Mar. 22, 1993, abandoned, which is a continuation-in-part of Ser. No. 716,917, Jun. 18, 1991, abandoned, which is a continuation-in-part of Ser. No. 615,430, Nov. 16, 1990, abandoned, and Ser. No. 38,517, Mar. 29, 1993, abandoned, which is a division of Ser. No. 614,912, Nov. 16, 1990, Pat. No. 5,226,914, and Ser. No. 38,512, Mar. 29, 1993, abandoned, which is a division of Ser. No. 614,915, Nov. 16, 1990, Pat. No. 5,197,985.

[51] Int. Cl.$^6$ ............................. C12N 5/00; C11N 5/02
[52] U.S. Cl. ................. 424/93.7; 435/366; 435/372
[58] Field of Search ................ 424/93.7; 435/372, 435/366

[56] References Cited

U.S. PATENT DOCUMENTS

| | | | |
|---|---|---|---|
| 3,968,567 | 7/1976 | Nevins | 32/15 |
| 4,254,226 | 3/1981 | Eisenger et al. | 435/240 |
| 4,430,760 | 2/1984 | Smestad | 3/1.9 |
| 4,481,946 | 11/1984 | Altshuler et al. | 604/4 |
| 4,486,188 | 12/1984 | Altshuler et al. | 604/4 |
| 4,596,574 | 6/1986 | Urist | 623/16 |
| 4,609,551 | 9/1986 | Caplan et al. | 424/95 |
| 4,642,120 | 2/1987 | Nevo et al. | 623/16 |
| 4,714,680 | 12/1987 | Civin | 435/240.25 |
| 4,721,096 | 1/1988 | Naughton et al. | 128/1 R |
| 4,846,835 | 7/1989 | Grande | 623/11 |
| 4,904,259 | 2/1990 | Itay | 623/16 |
| 5,053,050 | 10/1991 | Itay | 623/16 |
| 5,197,985 | 3/1993 | Caplan et al. | 623/16 |
| 5,206,023 | 4/1993 | Hunziker | 424/423 |
| 5,226,914 | 7/1993 | Caplan et al. | 623/16 |

OTHER PUBLICATIONS

Franzen et al., *Differentiation*, 36:199–210 (1987).
Goshima et al., *Clin. Orthop. & Rel. Res.*, 269: 274–283 (1991).
Goshima et al., *Clin. Orthop.* 262: 298–311 (1991).
Nakahara et al., *J. Orthop. Res.*, 9:465–476.
Linsenmeyer et al., *Biochem. Biophys. Res. Comm.*, 92 (2): 440–446 (1980).
Ashton et al., *Calcif. Tissue Int.*, 36: 83–86 (1984).
Bruder et al., *Bone and Mineral*, 11: 141–151 (1990).
Goding et al., *Monoclonal Antibodies: Principles and Practice*, Academic Press (NY), pp. 56–97 (1983).
Hoerl et al., *J. Cell. Biochem.*, 0(10 Part C):98 (1986).
Wang et al., *Cell Prolif.*, 26: 55–56 (1993).
Kipps et al., in Weir (Ed.), *Handbook of Expt'l Immunol*, Blackwell Scientific Publ. (London), vol. 4, pp. 108.1–108.9 (1986).
Harlow et al., *Antibodies: a Laboratory Manual* (vol. 4), Cold Spring Harbour, pp. 153–154, 392–393 and 578–581 (1988).
Lazarus et al., *ASBMT Abstract* (unpub.), Jan. 26, 1995.
Bruder et al., *J. Cell Biochem.*, 56: 283–294 (1994).
Alexander et al., *J. Cell. Biol.*, 118: 727–739 (1992).
Bibb et al., *J. Deaf. Res.*, 71(11): 1816–1821 (1992).
Ashton, et al., *Bone*, 6:313–319 (1985).
Caplan, *J. Orthoped. Res.*, 9(5): 641–650 (1991).
Smyth et al., *J. Cell Science*, 106: 1–9 (1993).
Beresford, in *Clin. Orthoped. and Related Res.*, No. 240, pp. 270–280 (1989).
Quinones, *Am. J. Ped. Hematol/Oncol.*, 15(1): 3–17 (1993).
ATCC Catalog (7th Ed.), p. 144 (1992).
Haynesworth et al., *Bone*, 13: 69–80 (1992).
Haynesworth et al., *Bone*, 13: 81–88 (1992).
Yoneda et al., *Science*, 213: 563–565 (1981).
Gibco Catalog, pp. 12, 15, 16, 55, 199, 202 and 203 (1990).
Nakahara et al., *Science*, 213: 563–565 (1981).
Freshney, *Culture of Animal Cells*, A.R. Liss Suc., pp. 162–165 and 187–190 (1987).
Sparks et al., *Cancer Res.*, 46: 5132–5319 (1986).
Aubin et al., *J. Cell Biol.*, 92: 452–461 (1982).

*Primary Examiner*—Leon B. Lankford, Jr.
*Attorney, Agent, or Firm*—Charles J. Herron; Elliot M. Olstein

[57] ABSTRACT

Isolated human mesenchymal stem cells, a method for isolating, purifying, and culturally expanding human mesenchymal stem cells (i.e. mesenchymal stem cells or "MSCs"), and characterization of (including by cytokine expression profiling) and uses, particularly research reagent, diagnostic and therapeutic uses for such cells. The stem cells can be culture expanded without differentiating. Monoclonal antibodies specific for human mesenchymal stem cells and the monoclonal hybridoma cell lines (ATCC nos. 10743–10745) that synthesize and secrete these monospecific antibodies, and uses of the monoclonal antibodies for diagnostic and/or therapeutic purposes.

27 Claims, 11 Drawing Sheets
(1 of 11 drawing(s) Filed in Color)

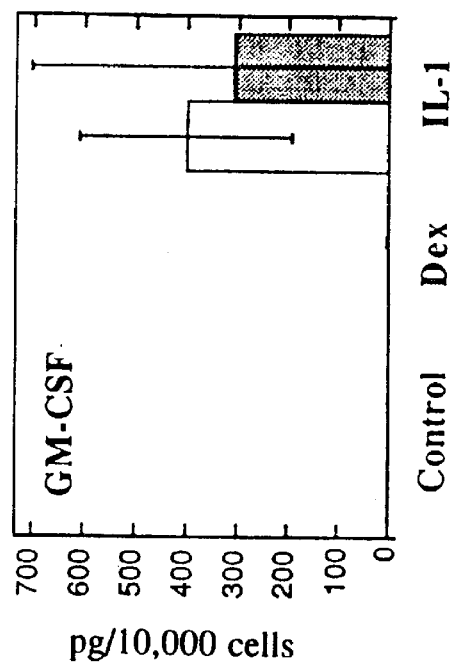
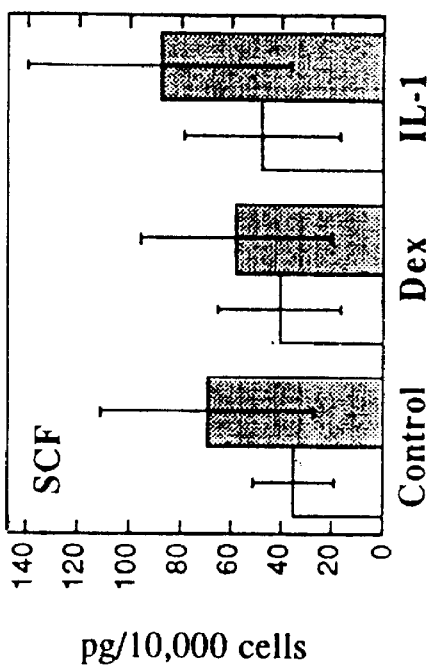
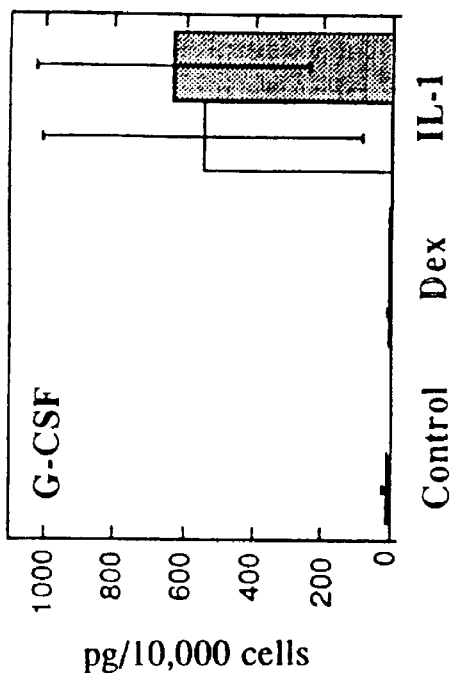
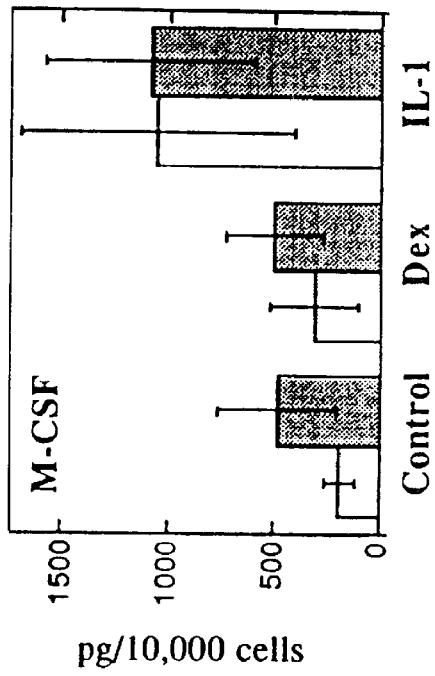

CONNECTIVE TISSUE REGENERATION USING HUMAN MESENCHYMAL STEM CELL PREPARATIONS

This is a continuation-in-part of U.S. Ser. No. 08/193,262, filed Feb. 8, 1994 (U.S. Pat. No. 5,486,359 issued on Jan. 23, 1996), which is a continuation-in-part of U.S. Ser. No. 08/034,272, filed Mar. 22, 1993 (abandoned), which is a continuation-in-part of U.S. Ser. No. 07/716,917 filed Jun. 18, 1991 (abandoned), which is a continuation-in-part of U.S. Ser. No. 07/615,430 filed Nov. 16, 1990 (abandoned); of U.S. Ser. No. 08/038,517, filed Mar. 29, 1993 (abandoned), which is a divisional of U.S. Ser. No. 07/614,912, filed Nov. 16, 1990 (U.S. Pat. No. 5,226,914 issued on Jul. 13, 1993); and of U.S. Ser. No. 08/038,512, filed Mar. 29, 1993 (abandoned), which is a divisional of 07/614,915, filed Nov. 16, 1990 (U.S. Pat. No. 5,197,985 issued on Mar. 30, 1993).

The present invention is directed to isolated and purified human mesenchymal stem cells, to a method for isolating, purifying, and culturally expanding human mesenchymal stem cells (i. e. mesenchymal stem cells or "MSCs"), and to characterization of and uses for such cells.

Further, the present invention is directed to monoclonal antibodies that are specific for human mesenchymal stem cells (i.e. mesenchymal stem cells). In addition, the invention is directed to the monoclonal hybridoma cell lines that synthesize and secrete these monospecific antibodies, and the use of the monoclonal antibodies for diagnostic and/or therapeutic purposes.

The present invention is also directed to various methods and devices for enhancing the implantation and differentiation of mesenchymal stem cells.

The present invention is also directed to various methods and devices for treating skeletal and other connective tissue disorders. The methods and devices of the invention utilize isolated mesenchymal progenitor cells which, under certain conditions, can be induced to differentiate into different types of desired connective tissue, such as into bone or cartilage forming cells.

Mesenchymal stem cells are the formative pluripotential blast cells found inter alia in bone marrow, blood, dermis and periosteum that are capable of differentiating into any of the specific types of mesenchymal or connective tissues (i.e. the tissues of the body that support the specialized elements; particularly adipose, osseous, cartilaginous, elastic, and fibrous connective tissues) depending upon various influences from bioactive factors, such as cytokines. Although these cells are normally present at very low frequencies in bone marrow, the inventors of the present invention have discovered a process for isolating, purifying, and greatly replicating these cells in culture, i.e. in vitro.

In one aspect, the present invention is directed to human mesenchymal stem cells isolated from a tissue specimen and the method of their isolation.

Homogeneous human mesenchymal stem cell compositions are provided which serve as the progenitors for all mesenchymal cell lineages. MSCs are identified by specific cell surface markers which are identified with unique monoclonal antibodies. The homogeneous MSC compositions are obtained by positive selection of adherent marrow or periosteal cells which are free of markers associated with either hematopoietic cell or differentiated mesenchymal cells. These isolated mesenchymal cell populations display epitopic characteristics associated with only mesenchymal stem cells, have the ability to regenerate in culture without differentiating, and have the ability to differentiate into specific mesenchymal lineages when either induced in vitro or placed in vivo at the site of damaged tissue.

In order to obtain subject human mesenchymal stem cells, it is necessary to isolate rare pluripotent mesenchymal stem cells from other cells in the bone marrow or other MSC source. Bone marrow cells may be obtained from iliac crest, femora, tibiae, spine, rib or other medullary spaces. Other sources of human mesenchymal stem cells include embryonic yolk sac, placenta, umbilical cord, fetal and adolescent skin, and blood.

The method of their isolation comprises the steps of providing a tissue specimen containing mesenchymal stem cells, adding cells from the tissue specimen to a medium which contains factors that stimulate mesenchymal stem cell growth without differentiation and allows, when cultured, for the selective adherence of only the mesenchymal stem cells to a substrate surface, culturing the specimen-medium mixture, and removing the non-adherent matter from the substrate surface.

In another aspect, the present invention relates to a medium for isolating human mesenchymal stem cells from a tissue specimen, wherein the medium is comprised of factors which stimulate mesenchymal stem cell growth without differentiation and allows, when cultured, for the selective adherence of only the mesenchymal stem cells to a substrate surface.

In an additional aspect, the invention is directed to a method for culture expanding the isolated and/or purified mesenchymal stem cells, e.g., marrow, blood, periosteum or dermis derived. The method comprises the steps of providing a tissue specimen containing mesenchymal stem cells, adding cells from the specimen to a medium which contains factors that stimulate mesenchymal stem cell growth without differentiation and allows, when cultured, for the selective adherence of only the mesenchymal stem cells to a substrate surface, culturing the tissue specimen-medium mixture, removing the non-adherent matter from the substrate surface by replacing the medium with a fresh medium of the same composition, and, allowing the isolated adherent mesenchymal stem cells to culture expand. It has been found that the differential and/or reparative potential of the culture-expanded mesenchymal stem cells is maintained during culture expansion under specific conditions.

In a further aspect, the present invention relates to a kit for isolating mesenchymal stem cells from a tissue specimen. The kit is comprised of a medium containing factors which stimulate the growth of the mesenchymal stem cells without differentiation and allow, when cultured, for the selective adherence of only the mesenchymal stem cells to a substrate surface; and, a device having such a substrate surface.

The inventors have also discovered that certain factors, such as mechanical, cellular, and biochemical stimuli can be utilized in order to induce differentiation of the mesenchymal stem cells into specific types of desired connective tissue, such as bone forming cells, etc.

In another aspect, the present invention provides monoclonal antibodies that are specific to cell surface determinants of the human mesenchymal stem cells. Since there were, prior to the present invention, no known specific markers for mesenchymal stem cells, such as enzyme activity, extracellular matrix molecules, or characteristic morphology, the monoclonal antibodies of the present invention (which recognize cell surface determinants on mesenchymal stem cells but not certain other cells such as hemopoietic cells) provide effective monospecific probes for positively selecting, identifying, quantifying, and/or purifying mesenchymal stem cells from tissue specimens such as bone marrow, blood (including peripheral blood), periosteum and dermis.

While the production of monoclonal antibodies by the fusion of spleen cells from immunized mice and myeloma cells grown in continuous culture has been previously described, e.g. Kohler, et al. in Nature, Vol. 256, pp. 495–497 (1975), Kohler, et al. in *European Journal of Immunology*, Vol. 6, pp. 511–519 (1976), Galfre, et al. in *Nature*, Vol. 266, pp. 550–552 (1977), and in the text *Monoclonal Antibodies, Hybridomas: A New Dimension in Biological Analysis*, R. Kennett, T. McKearn, K. Bechtol, Eds., Plenum Press, New York, and London, (1980), and the techniques for the chemical selection of hybridomas arising from such a fusion, and the subsequent isolation of single antibody secreting cell clones for the production of the monoclonal antibodies are also known, no cell lines have ever been produced capable of synthesizing and secreting monoclonal antibodies which selectively bind mesenchymal stem cells and not hemopoietic or other closely related cells.

In still another aspect, the present invention relates to hybridomas which synthesize and secrete monoclonal antibodies that are specific for human mesenchymal stem cells. The antibodies recognize an antigen that is present on the cell surface of mesenchymal stem cells but not on hemopoietic cells. Moreover, the present invention is also directed to the monoclonal antibodies produced by the hybridomas of the invention, as well as the particular method utilized for producing both the hybridomas and the specific monoclonal antibodies.

In an additional aspect, the present invention is directed to various methods of utilizing human mesenchymal stem or progenitor cells and the monoclonal antibodies produced by the present invention for therapeutic and/or diagnostic purposes. For example, human mesenchymal stem or progenitor cells find use in: (1) regenerating mesenchymal tissues which have been damaged through acute injury, abnormal genetic expression or acquired disease; (2) treating a host with damaged mesenchymal tissue by removal of small aliquots of bone marrow, isolation of their mesenchymal stem cells and treatment of damaged tissue with MSCs combined with a biocompatible carrier suitable for delivering MSCs to the damaged tissues site(s); (3) producing various mesenchymal tissues; (4) detecting and evaluating growth factors relevant to MSC self-regeneration and differentiation into committed mesenchymal lineages; (5) detecting and evaluating inhibitory factors which modulate MSC commitment and differentiation into specific mesenchymal lineages; and (6) developing mesenchymal cell lineages and assaying for factors associated with mesenchymal tissue development.

The present invention is also directed to methods of utilizing the mesenchymal progenitor or stem cells for correcting or modifying connective tissue disorders, such as the regeneration of missing or damaged skeletal tissue, enhancing the implantation of various plastic or metal prosthetic devices through the attachment of the isolated mesenchymal progenitor or stem cells onto the porous surfaces of the prosthetic devices or various tri-calcium or hydroxyapatite ceramic vehicles or carriers, which, upon the activation and subsequent differentiation of the mesenchymal progenitor or stem cells, produce natural osseous or viscous bridges.

In addition, the present invention relates to various methods and devices for utilizing the mesenchymal progenitor or stem cells in order to enhance hemopoietic cell production. In this regard, one embodiment of the invention is directed to methods for using composite grafts of mesenchymal progenitor or stem cells to augment the rate of hemopoietic cell reserve during bone marrow transplantation. An additional embodiment of the invention concerns various methods for using composite grafts of mesenchymal progenitor or stem cells and ceramics implanted into hosts, such as into subcutaneous sites in nude mice, as catalysts for the production of a reservoir of hemopoietic stem cells.

In another aspect, the present invention relates to a method for repairing connective tissue damage. The method comprises the steps of applying a mesenchymal stem or progenitor cell-containing extract to an area of connective tissue damage under conditions suitable for differentiating the cells into the type of connective tissue necessary for repair.

In a further aspect, the present invention is directed to a method for enhancing the implantation of a prosthetic device into skeletal tissue. The method comprises the steps of adhering mesenchymal stem or progenitor cells onto the connective surface of a prosthetic device, and implanting the prosthetic device containing these mesenchymal cells under conditions suitable for differentiating the cells into the type of skeletal or connective tissue needed for implantation.

In an additional aspect, the present invention concerns various methods and devices for using these mesenchymal stem or progenitor cells in order to enhance the production of hemopoietic cells. For example, one of the embodiments of the present invention is directed to a method for using composite grafts of mesenchymal stem or progenitor cells to augment the rate of hemopoietic cell rescue during bone marrow transplantation. A further embodiment of the invention concerns a method for using composite grafts of mesenchymal stem or progenitor cells and ceramics which are implanted into hosts in order to act as catalysts for the production of an ectopic reservoir of hemopoietic stem cells.

In another aspect, the present invention is directed to various devices and factors which have been developed in order to induce the mesenchymal stem or progenitor cells to differentiate into specific types of desired phenotypes, such as bone or cartilage forming cells. For example, the inventors have found that various porous tri-calcium or hydroxyapatite ceramic devices can be utilized as vehicles or carriers for the mesenchymal stem or progenitor cells when implanted into skeletal defects thereby permitting and/or promoting the differentiation of the cells into skeletal tissue.

More particularly, one embodiment of the invention is directed to a method for using a porous ceramic composition comprised of tri-calcium phosphate or hydroxyapatite or combinations of the two, as a vehicle or carrier for mesenchymal stem or progenitor cells, which, when implanted into skeletal defects, promotes the differentiation of the cells into skeletal tissue.

In a further aspect, the present invention is directed to a method for repairing skeletal defects. The method comprises the steps of providing a bone marrow specimen containing mesenchymal stem or progenitor cells, adding cells from the bone marrow specimen to a medium (i.e. "complete medium") which contains factors that stimulate mesenchymal stem or progenitor cell growth without differentiation and allows, when cultured, for the selective adherence of only the mesenchymal stem or progenitor cells to a substrate surface, culturing the bone marrow-medium mixture, removing the non-adherent matter from the substrate surface by replacing the medium with a fresh medium of the same composition, and, allowing the isolated adherent mesenchymal stem or progenitor cells to culturally expand. The culturally expanded mesenchymal stem or progenitor cells are then applied to a porous carrier, such as a porous calcium phosphate and/or hydroxyapatite ceramic block, which is subsequently implanted into the defective skeletal tissue. It has been found that through the use of the porous carrier containing the mesenchymal stem or progenitor cells, these mesenchymal cells fairly rapidly differentiate into bone producing cells. As a result, the method and device of the invention are an effective means for treating skeletal and other connective tissue disorders.

The file of this patent includes at least one drawing executed in color.

The following is a brief description of the drawings which are presented only for the purposes of further illustrating the invention and not for the purposes of limiting the same.

Figure 2A:
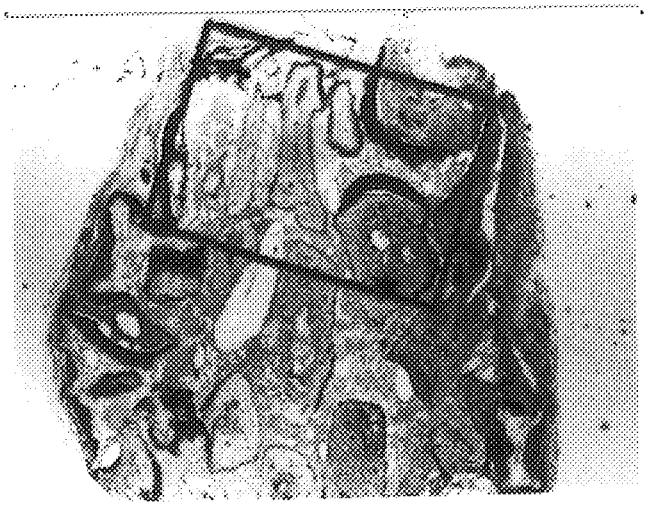
Figure 2B:
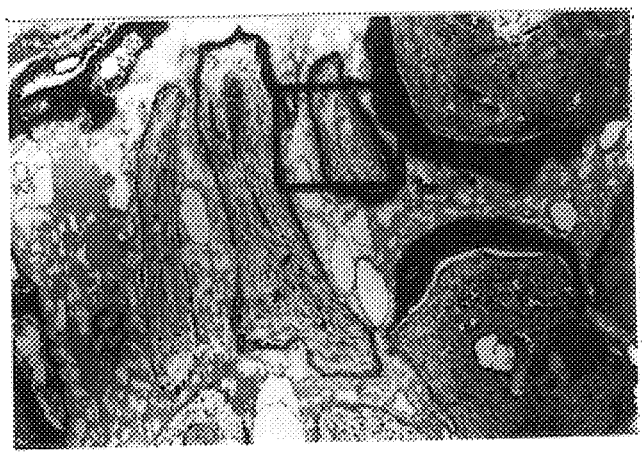
Figure 2C:
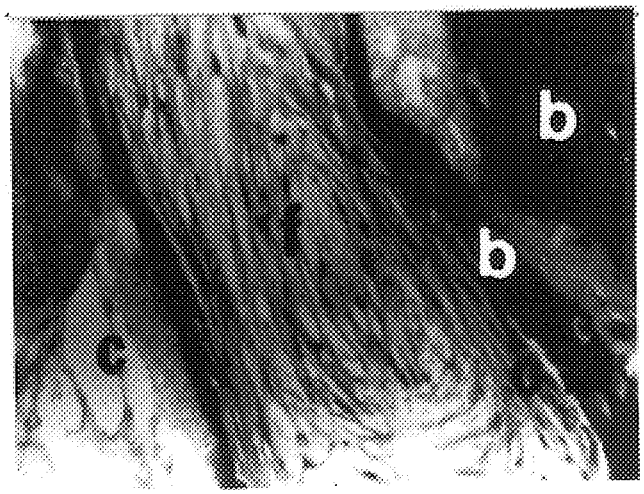
Figure 3A:
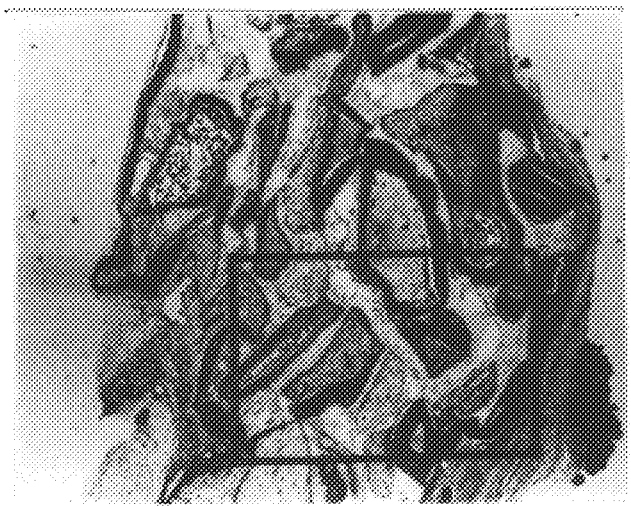
Figure 3B:
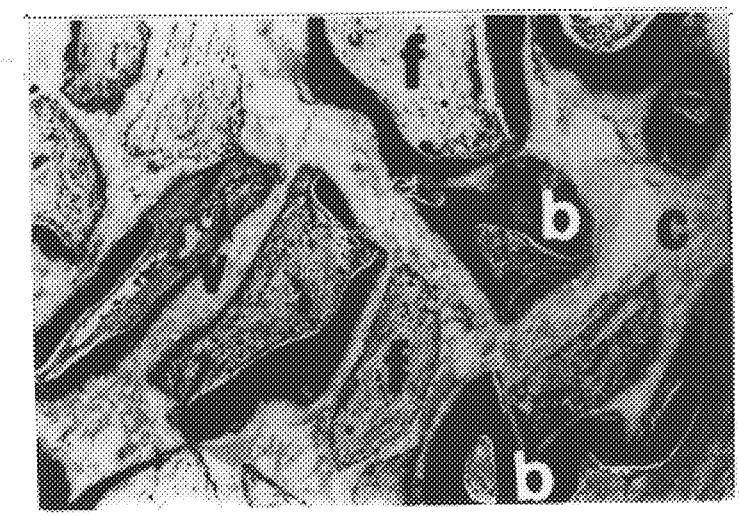
Figure 4A:
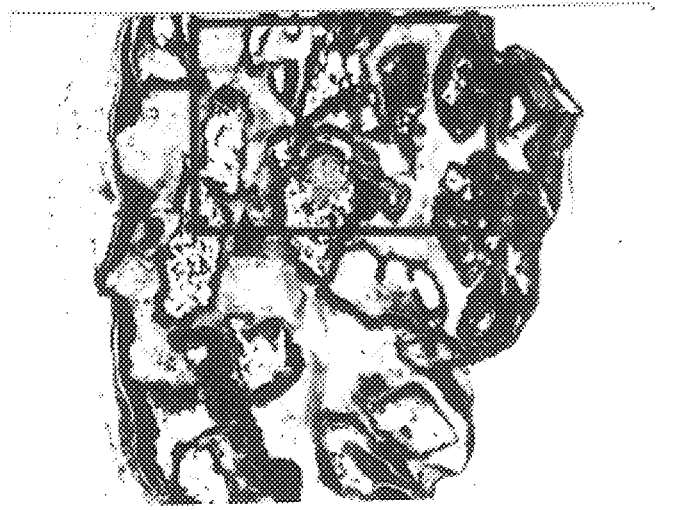
Figure 4B:
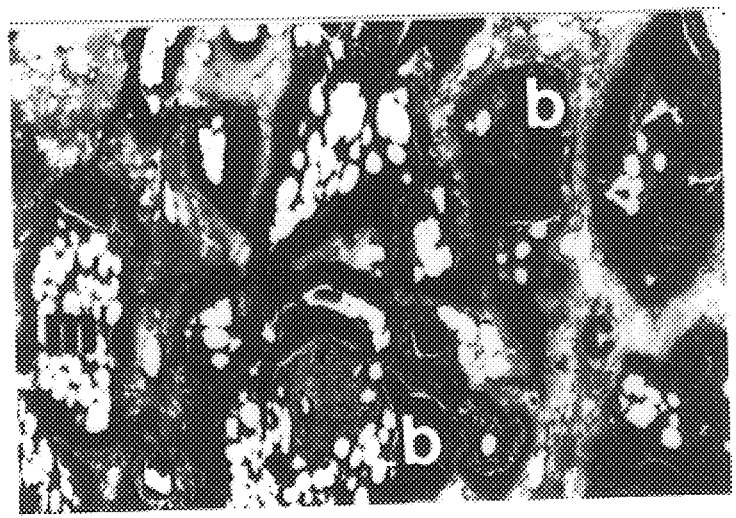

FIG. 1 is a phase contrast photomicrograph of a monolayer culture of fibroblast-like cells derived from human marrow (100×);

FIGS. 2A–2C are a series of photomicrographs (Mallory Heidehain Staining) of a histological section of a composite containing cultured human marrow fibroblasts and ceramic after two weeks of incubation in a nude mouse; FIG. 2A shows the formation of new bone (B) lining the pores of the ceramic ghost (G) (40×); FIG. 2B indicates that the fibrous tissue (F) was present in most of the pores whereas host vascular (V) was present in only some pores but not others (100× of boxed area in FIG. 2A); FIG. 2C illustrates that the osteocytes (C) were clearly visibly embedded within the bone matrix. Putative osteoblasts (OB) lined the inner surface of the new bone matrix (400× of boxed area in FIG. 2B);

FIGS. 3A–3B are a series of photomicrographs (Mallory Heidehain staining) of a histological section of a composite containing cultured human marrow fibroblasts in ceramic after three weeks of incubation in a nude mouse; FIG. 3A indicates that bone (B) was observed lining a greater number of pores of the ceramic ghost (G) than in FIG. 2 (2 week incubation) (40×); FIG. 3B demonstrates that the fibrous tissue (F) still remained in the inner spaces of most of the pores. In addition, host vasculature (V) was also present in some pores (100× of boxed area in FIG. 3A);

FIGS. 4A–4B are two photomicrographs (Mallory Heidenhain staining) of a histological section of cultured human marrow fibroblasts in ceramic after six weeks of incubation in a nude mouse; FIG. 4A indicates that bone (B) was observed lining most of the pores of the ceramic ghost (G) (40×); FIG. 4B shows the fibrous tissue (F) observed in the inner spaces of a few pores, however, marrow (M) and vasculature (V) had replaced the fibrous tissue in a majority of the pores (100× of the boxed area in FIG. 4A).

Figure 5:
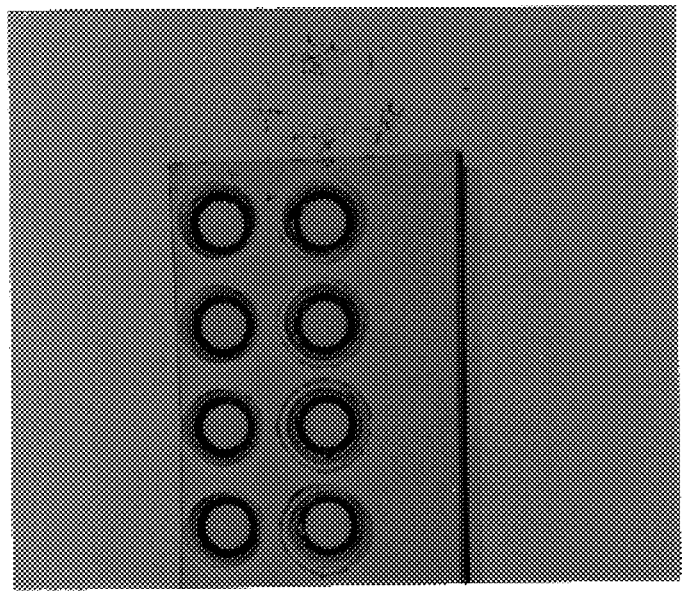

FIG. 5 is a photograph illustrating the positive results of the IgG ELISA assay of Example 2 (III) (A).

Figure 6A:
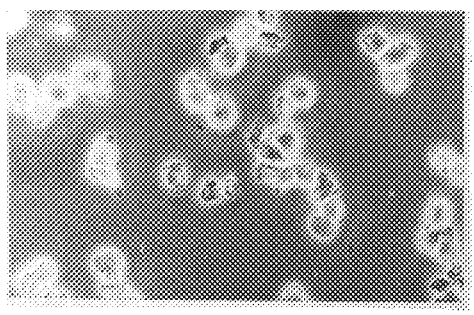
Figure 6B:
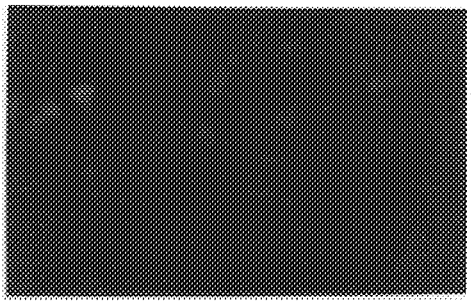
Figure 6C:
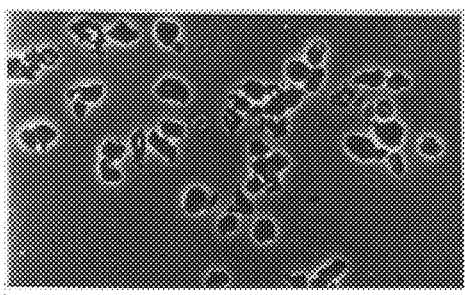
Figure 6D:
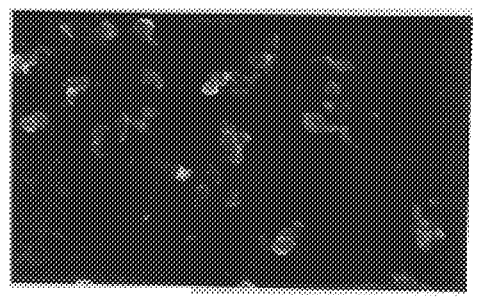
Figure 6E:
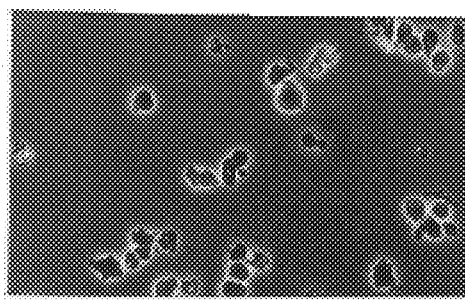
Figure 6F:
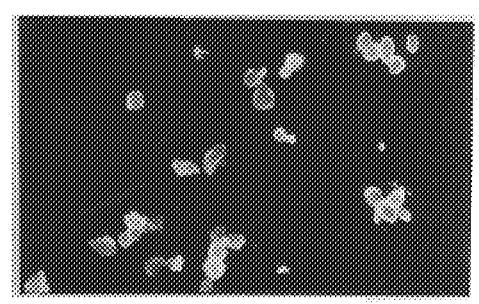
Figure 6G:
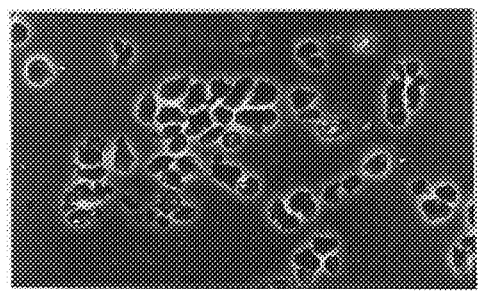
Figure 6H:
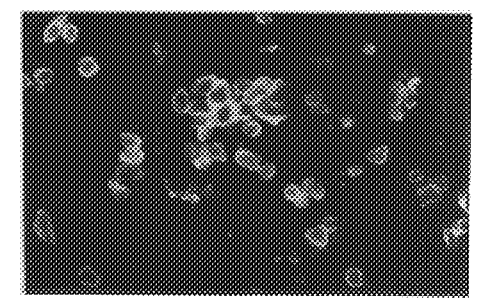

FIGS. 6A–6H are photomicrographs of a typical frozen section of pelleted culture expanded human marrow-derived cells by indirect immunofluorescence (400×). FIGS. 6A (phase) and 6B (fluorescence), 6C (phase) and 6D (fluorescence), and 6E (phase) and 6F (fluorescence), and 6G (phase), and 6H (fluorescence) represent SB-1 control, SH2, SH3, and SH4 antibodies which tested positive to specificity for IgG secretion and the specificity to frozen pelleted culture marrow cells.

Figure 7A:
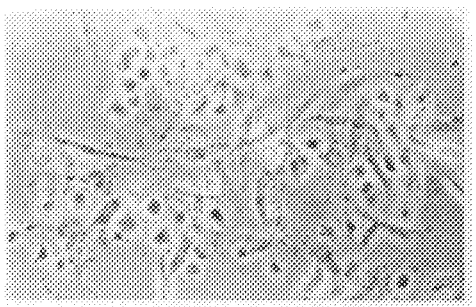
Figure 7B:
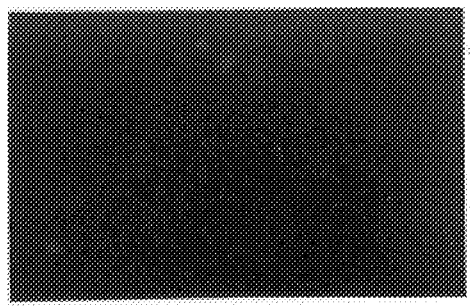
Figure 7C:
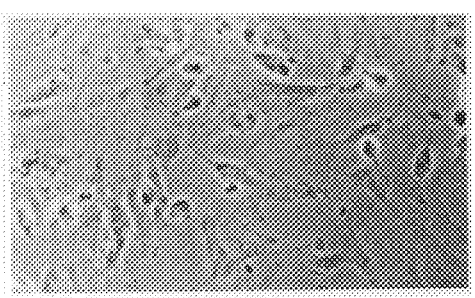
Figure 7D:
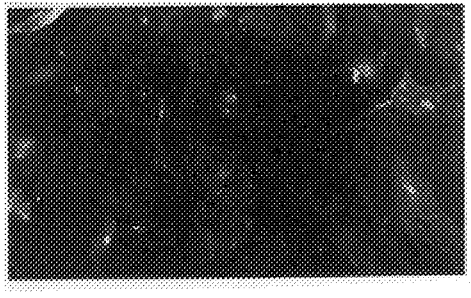
Figure 7E:
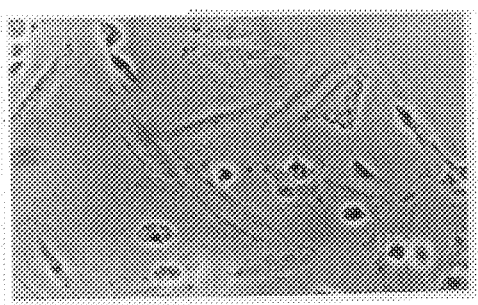
Figure 7F:
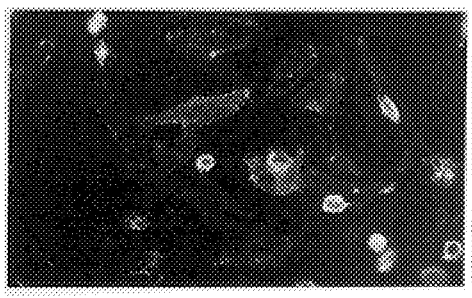
Figure 7G:
Figure 7H:

FIGS. 7A–7H are photomicrographs illustrating the typical positive results from the indirect immunofluorescence analysis of living cultured marrow-derived mesenchymal cells in micromass (400×). FIGS. 7A (phase) and 7B (fluorescence), 7C (phase) and 7D (fluorescence), and 7E (phase) and 7F (fluorescence), and 7G (phase) and 7H (fluorescence) represent SB-1 control, SH2, SH3, and SH4 antibodies which tested positive to specificity to living cultured marrow-derived human mesenchymal stem cells.

Figure 8:
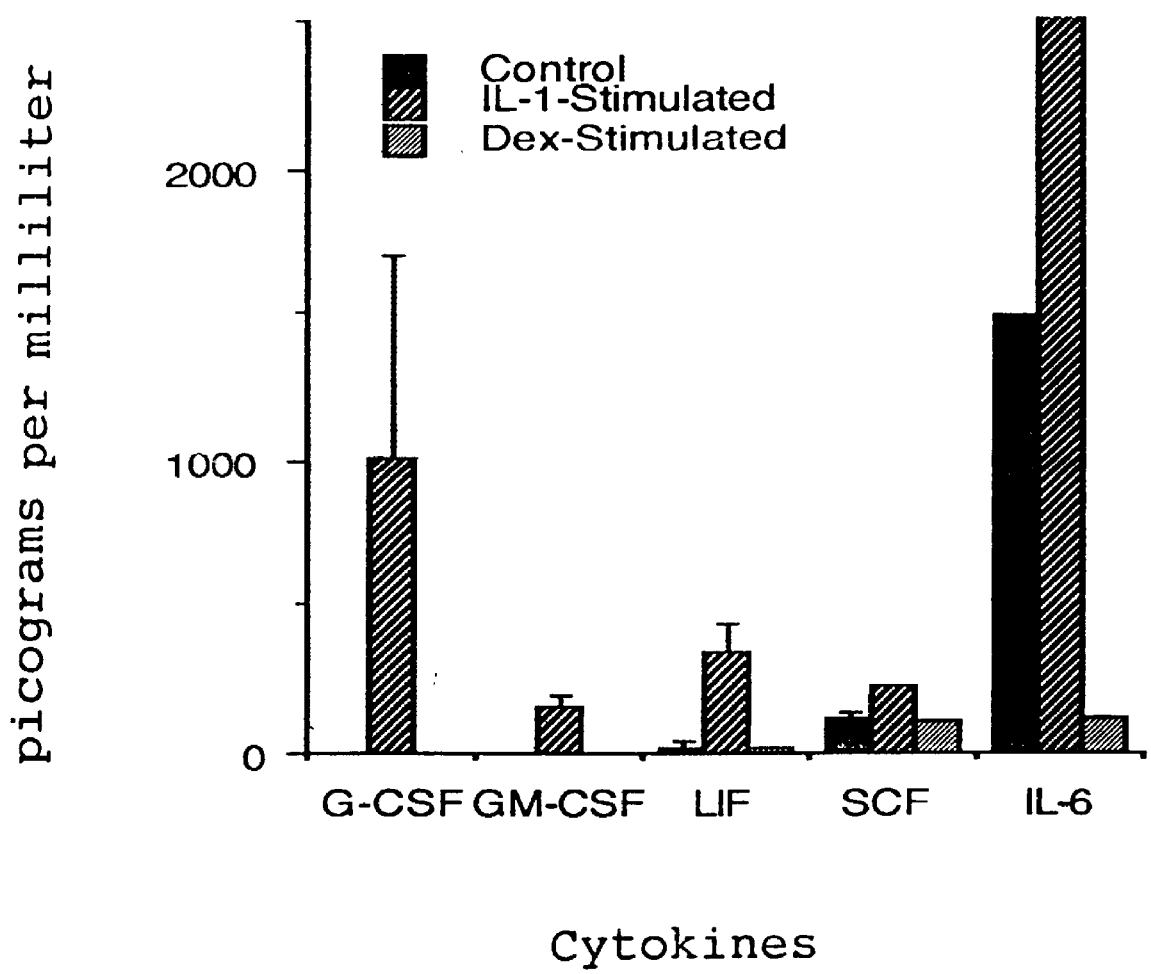

FIG. 8 graphically depicts the cytokines assayed and their levels of secretion by human mesenchymal stem cells as tested by the experiments reported in Example 4.

FIGS. 9A–D graphically depicts the effects of cytokines on stem cells.

Figure 10A:
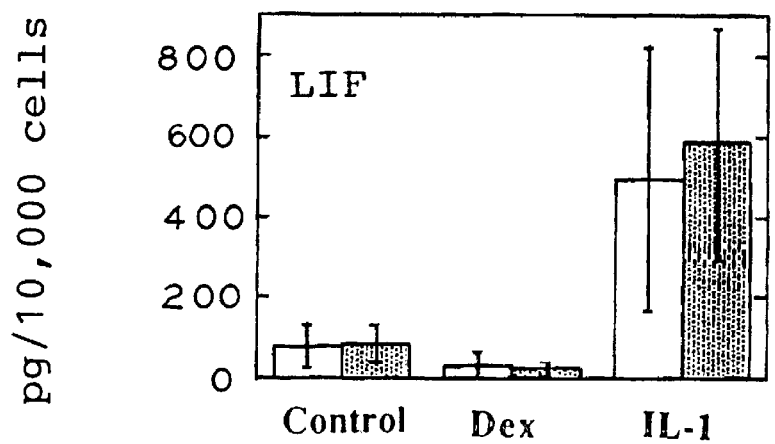
Figure 10B:
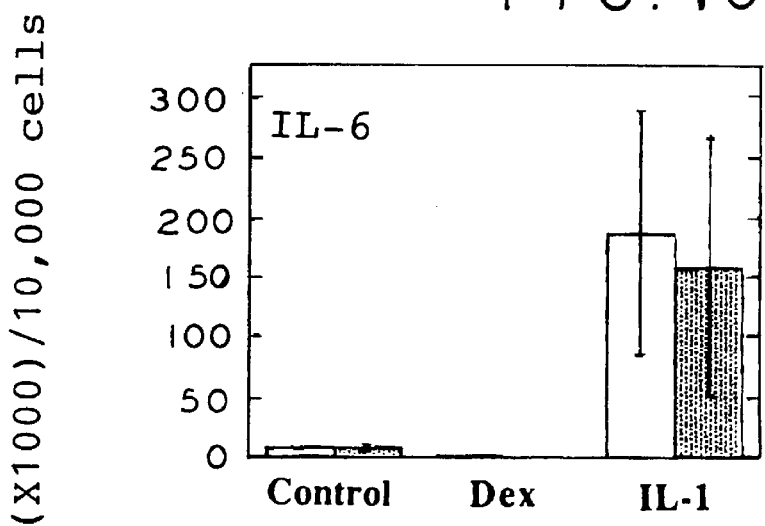
Figure 10C:
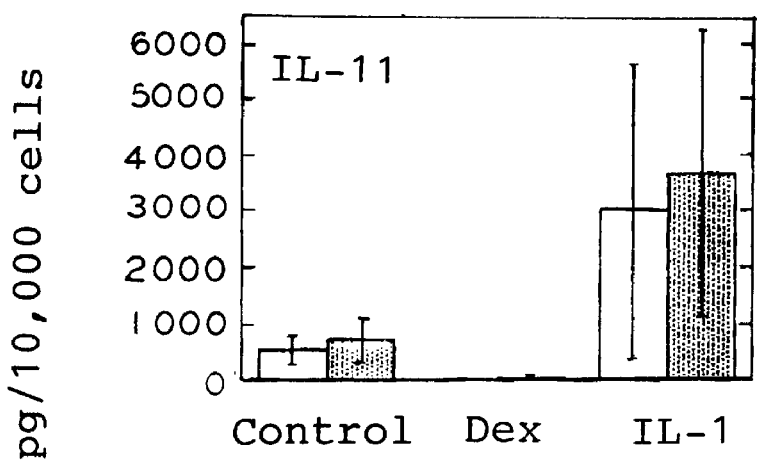

FIGS. 10A–C graphically depicts the effects of cytokines on stem cells.

Figure 11:
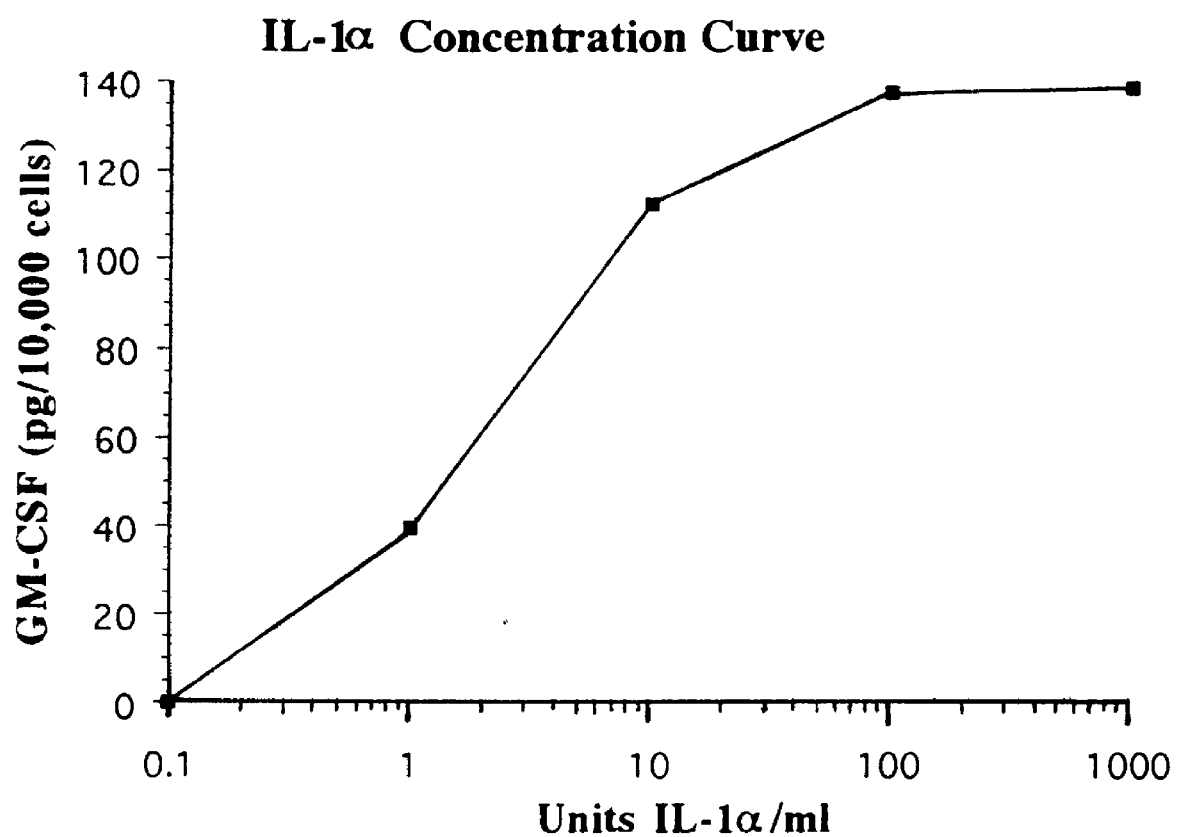

FIG. 11 graphically depicts the effects of cytokines on stem cells.

The present invention relates to the discovery that through a fairly detailed process, the progenitor cells to the various types of connective tissues can be isolated and purified from tissue such as bone marrow, blood (including peripheral blood), periosteum and dermis, and other tissues which have mesodermal origins. These cells are referred to by the inventors as human "mesenchymal stem cells" or "MSCs." In this regard, it has been found that although these progenitor mesenchymal stem cells are normally present in bone marrow, for example, in very minute amounts and that these amounts greatly decrease with age (i.e. from about 1/10,000 cells in a relatively young patient to as few as 1/2,000,000 in an elderly patient), human mesenchymal stem cells can be isolated from tissue and purified when cultured in a specific medium by their selective attachment, termed "adherence," to substrates.

Compositions having greater than 95%, usually greater than 98% of human mesenchymal stem cells can be achieved using the previously described technique for isolation, purification and culture expansion of MSCs. The desired cells in such compositions are identified as $SH2^+$, $SH3^+$, $SH4^+$ and $CD^-$ and are able to provide for both self renewal and differentiation into the various mesenchymal lineages. Ultimately, repair and regeneration of various mesenchymal tissue defects could be accomplished starting from a single mesenchymal stem cell.

In addition, it has also been found that the isolated and purified human mesenchymal stem cells can be grown in an undifferentiated state through mitotic expansion in a specific medium. These cells can then be harvested and activated to differentiate into bone, cartilage, and various other types of connective tissue by a number of factors, including mechanical, cellular, and biochemical stimuli. As a result, it has been determined that human mesenchymal stem cells possess the potential to differentiate into cells such as osteoblasts and chondrocytes, which produce a wide variety of mesenchymal tissue cells, as well as tendon, ligament and dermis, and that this potential is retained after isolation and for several population expansions in culture. Thus, by being able to isolate, purify, greatly multiply, and then activate the mesenchymal stem cells to differentiate into the specific types of mesenchymal cells desired, such as bone-forming osteoblast cells, etc., a highly effective process exists for treating skeletal and other connective tissue disorders.

The present invention is also directed to the in vitro production of monoclonal antibodies specific to the isolated, purified, and culture expanded mesenchymal stem cells described above, and the use of the monoclonal antibodies and associated hybridomas (i.e. the fused myeloma-lymphocyte cells which produce the monoclonal antibodies and associated hybridomas) for diagnostic and/or therapeutic purposes. The monoclonal antibodies can be utilized not only for identifying, enumerating, localizing, and isolating mesenchymal stem cells through various means such as immunofluorescence or fluorescence-activated cell sorting (FACS), but also for delivering various pharmaceutical products, etc.

A. Isolation & Purification of Human Mesenchymal Stem Cells

Bone marrow is the soft tissue occupying the medullary cavities of long bones, some haversian canals, and spaces between trabeculae of cancellous or spongy bone. Bone marrow is of two types: red, which is found in all bones in early life and in restricted locations in adulthood (i.e. in the spongy bone) and is concerned with the production of blood cells (i.e. hematopoiesis) and hemoglobin (thus, the red color); and yellow, which consists largely of fat cells (thus, the yellow color) and connective tissue.

As a whole, bone marrow is a complex tissue comprised of hematopoietic stem cells, red and white blood cells and their precursors, mesenchymal stem cells, stromal cells and their precursors, and a group of cells including fibroblasts, reticulocytes, adipocytes, and endothelial cells which form a connective tissue network called "stroma". Cells from the stroma morphologically regulate the differentiation of hematopoietic cells through direct interaction via cell surface proteins and the secretion of growth factors and are involved in the foundation and support of the bone structure. Studies using animal models have suggested that bone marrow contains "pre-stromal" cells which have the capacity to differentiate into cartilage, bone, and other connective tissue cells. (Beresford, J. N.: Osteogenic Stem Cells and the Stromal System of Bone and Marrow, *Clin. Orthop.,* 240:270, 1989). Recent evidence indicates that these cells, called pluripotent stromal stem cells or mesenchymal stem cells, have the ability to generate into several different types of cell lines (i.e. osteocytes, chondrocytes, adipocytes, etc.) upon activation. However, the mesenchymal stem cells are present in the tissue in very minute amounts with a wide variety of other cells (i.e. erythrocytes, platelets, neutrophils, lymphocytes, monocytes, eosinophils, basophils, adipocytes, etc.), and, in an inverse relationship with age, they are capable of differentiating into an assortment of connective tissues depending upon the influence of a number of bioactive factors.

As a result, the inventors have developed a process for isolating and purifying human mesenchymal stem cells from tissue prior to differentiation and then culture expanding the mesenchymal stem cells to produce a valuable tool for musculoskeletal therapy. The objective of such manipulation is to greatly increase the number of mesenchymal stem cells and to utilize these cells to redirect and/or reinforce the body's normal reparative capacity. The mesenchymal stem cells are harvested in great numbers and applied to areas of connective tissue damage to enhance or stimulate in vivo growth for regeneration and/or repair, to improve implant adhesion to various prosthetic devices through subsequent activation and differentiation, enhance hemopoietic cell production, etc.

Along these lines, various procedures are contemplated by the inventors for transferring, immobilizing, and activating the culture expanded, purified mesenchymal stem cells at the site for repair, implantation, etc., including injecting the cells at the site of a skeletal defect, incubating the cells with a prosthesis and implanting the prosthesis, etc. Thus, by isolating, purifying and greatly expanding the number of cells prior to differentiation and then actively controlling the differentiation process by virtue of their positioning at the site of tissue damage or by pretreating in vitro prior to their transplantation, the culture-expanded, undifferentiated mesenchymal stem cells can be utilized for various therapeutic purposes such as to elucidate cellular, molecular, and genetic disorders in a wide number of metabolic bone diseases, skeletal dysplasias, cartilage defects, ligament and tendon injuries and other musculoskeletal and connective tissue disorders.

In this regard, the present inventors have discovered that when the culturally-expanded mesenchymal cells are loaded into various porous carrier vehicles under certain conditions, the culturally-expanded mesenchymal cells have the ability to differentiate into bone-forming osteoblast cells, as opposed to cartilage forming cells. As a result, the isolated and culturally expanded marrow-derived mesenchymal cells can be utilized in certain porous vehicles or carriers, to produce the desired phenotype needed for connective tissue repair and/or the implantation of various prosthetic devices.

Along these lines, various procedures are contemplated by the inventors for transferring, immobilizing, and activating the mesenchymal stem or progenitor cells at the site for repair, implantation, etc., through the use of various porous ceramic vehicles or carriers, including injecting the cells into the porous ceramic vehicle or carrier at the site of a skeletal defect, incubating the cells with the porous ceramic vehicle or carrier attached to a prosthesis and implanting the carrier-prosthesis device, etc.

As more specifically indicated below in Example 1, the human mesenchymal stem cells isolated and purified in the present invention were derived, for example, from bone marrow obtained from a number of different sources, including plugs of femoral head cancellous bone pieces, obtained from patients with degenerative joint disease during hip or knee replacement surgery, and from aspirated marrow obtained from normal donors and oncology patients who have marrow harvested for future bone marrow transplantation. Although the harvested marrow was prepared for cell culture separation by a number of different mechanical isolation processes depending upon the source of the harvested marrow (i.e. the presence of bone chips, peripheral blood, etc.), the critical step involved in the isolation processes was the use of a specially prepared medium that contained agents which allowed for not only mesenchymal stem cell growth without differentiation, but also for the direct adherence of only the mesenchymal stem cells to the plastic or glass surface area of the culture dish. By producing a medium which allowed for the selective attachment of the desired mesenchymal stem cells which were present in the marrow samples in very minute amounts, it was possible to separate the mesenchymal stem cells from the other cells (i.e. red and white blood cells, other differentiated mesenchymal cells, etc.) present in the bone marrow.

Several media were prepared which were particularly well suited to the desired selective attachment and are referred to herein as "complete media" when supplemented with serum as described below. One such medium is an augmented version of Dulbecco's Modified Eagle's Medium (DMEM), which is well known and readily commercially available. The formulation of standard DMEM is as follows:

Dulbecco's Modified Eagle's Medium

| COMPONENT | mg/L |
| --- | --- |
| Amino Acids: | |
| L-Arginine Hcl | 84.00 |
| L-Cystine | |
| L-Cystine 2HC1 | 62.57 |
| L-Glutamine | 584.00 |
| Glycine | 30.00 |
| L-Histidine Hcl.$H_2O$ | 42.00 |
| L-Isoleucine | 105.00 |
| L-Leucine | 105.00 |
| L-Lysine-HCl | 146.00 |
| L-Methionine | 30.00 |

-continued

| COMPONENT | mg/L |
|---|---|
| L-Phenylalanine | 66.00 |
| L-Serine | 42.00 |
| L-Threonine | 95.00 |
| L-Tryptophan | 16.00 |
| L-Tyrosine | — |
| L-Tyrosine 2Na.2H$_2$O | 103.79 |
| L-Valine | 94.00 |
| Inorganic Salts | |
| CaCl$_2$ (anhyd.) | 200.00 |
| Fe(NO$_3$)$_2$.9H$_2$O | 0.10 |
| KCl | 400.00 |
| MgSO$_4$ (anhyd.) | 97.67 |
| NaCl | 6,400.00 |
| NaHCO$_2$ | |
| Na$_2$HPO$_4$H$_2$O$_6$ | 125.00 |
| Other Components: | |
| D-Glucose | 1,000.00 |
| Phenol red | 15.00 |
| HEPES | |
| Sodium pyruvate | 110.00 |
| Vitamins: | |
| D-Ca pantothenate | 4.00 |
| Choline chloride | 4.00 |
| Folic acid | 4.00 |
| i-Inositol | 7.20 |
| Niacinamide | 4.00 |
| Pyridoxal-Hcl | 4.00 |
| Riboflavin | 0.40 |
| Thiamine-Hcl | 4.00 |

The commercial formulation is supplemented with 3700 mg/l of sodium bicarbonate and 10 ml/l of 100× antibiotic-antimycotic containing 10,000 units of penicillin (base), 10,000 μg of streptomycin (base) and 25 μg of amphotericin B/ml utilizing penicillin G (sodium salt), streptomycin sulfate, and amphotericin B as FUNGIZONE® in 0.85% saline.

The medium described above is made up and stored in 90 ml per 100 ml or 450 ml per 500 ml bottles at 4° C. until ready to use. For use, 10 ml or 50 ml of fetal bovine serum (from selected lots) to the bottles of media to give a final volume of 10% serum. The medium is warmed to 37° C. prior to use.

In this regard, it was also found that BGJ$_b$ medium (Gibco, Grand Island, N.Y.) with tested and selected lots of 10% fetal bovine serum (J.R. Scientific, Woodland, Calif., or other suppliers) was well suited for use in the invention. This medium, which was also a "complete medium", contained factors which also stimulated mesenchymal stem cell growth without differentiation and allowed for the selective attachment through specific protein binding sites, etc. of only the mesenchymal stem cells to the plastic surfaces of Petri dishes.

The principal components of the BGJ$_b$ Medium (Fitton-Jackson Modification) utilized to formulate this complete medium are set forth below:

| COMPONENT | 320-2591 1X Liquid (mg/L) |
|---|---|
| Inorganic Salts: | |
| NaH$_2$PO$_4$.H$_2$O | 90.00 |
| MgSO$_4$.7H$_2$O | 200.00 |
| KCl | 400.00 |
| KH$_2$PO$_4$ | 160.00 |
| NaHCO$_3$ | 3500.00 |
| NaCl | 5300.00 |
| Other Components: | — |
| Calcium Lactate | 550.00 |
| D-Glucose | 10,000.00 |
| Phenol red | 20.00 |
| Sodium acetate | 50.00 |
| Amino Acids: | — |
| L-Alanine | 250.00 |
| L-Arginine | 175.00 |
| L-Arginine Hcl | — |
| L-Aspartic acid | 150.00 |
| L-Cysteine Hcl.H$_2$O | 101.00 |
| L-Glutamine | 200.00 |
| Glycine | 800.00 |
| L-Histidine | 150.00 |
| L-Histidine Hcl.H$_2$O | — |
| L-Isoleucine | 30.00 |
| L-Leucine | 50.00 |
| L-Lysine | 240.00 |
| L-Lysine HCl | — |
| L-Methionine | 50.00 |
| L-Phenylalanine | 50.00 |
| L-Proline | 400.00 |
| L-Serine | 200.00 |
| L-Threonine | 75.00 |
| L-Tryptophan | 40.00 |
| L-Tyrosine | 40.00 |
| DL-Valine | 65.00 |
| L-Valine | — |
| Vitamins: | |
| α-tocopherol phosphate (disodium salt) | 1.00 |
| Ascorbic acid | 50.00 |
| Biotin | 0.20 |
| D-Ca pantothenate | 0.20 |
| Choline chloride | 50.00 |
| Folic acid | 0.20 |
| i-Inositol | 0.20 |
| Nicotinamide | 20.00 |
| Para-aminobenzoic acid | 2.00 |
| Pyridoxal phosphate | 0.20 |
| Riboflavin | 0.20 |
| Thiamine HCl | 4.00 |
| Vitamin B$_{12}$ | 0.04 |

In addition, it was also found that the medium F-12 Nutrient Mixture (Ham) (Gibco, Grand Island, N.Y.) exhibited the desired properties for selective mesenchymal stem cell separation. The principal components of the F-12 Nutrient Mixture (Ham) "complete medium" are as follows:

| COMPONENT | 320-1765 1X Liquid (mg/L) | 430-1700 Powder (mg/L) |
|---|---|---|
| Inorganic Salts: | | |
| CaCl$_2$ (anhyd.) | — | 33.22 |
| CaCl$_2$.2H$_2$O | 44.00 | — |
| CuSO$_4$.5H$_2$O | 0.00249 | 0.00249 |
| FeSO$_4$.7H$_2$O | 0.834 | 0.834 |
| KCl | 223.60 | 223.60 |
| KH$_2$PO$_4$ | — | — |
| MgCl$_2$ (anhyd.) | — | 57.22 |
| MgCl$_2$.6H$_2$O | 122.00 | — |
| MgSO$_4$ (anhyd.) | — | — |
| MgSO$_4$.7H$_2$O | — | — |
| NaCl | 7599.00 | 7599.00 |
| NaHCO$_3$ | 1176.00 | — |
| Na$_2$HPO$_4$ (anhyd.) | — | 142.04 |

-continued

| COMPONENT | 320-1765 1X Liquid (mg/L) | 430-1700 Powder (mg/L) |
|---|---|---|
| $Na_2HPO_4.7H_2O$ | 268.00 | — |
| $ZnSO_4.7H_2O$ | 0.863 | 0.863 |
| Other Components: | | |
| D-Glucose | 1802.00 | 1802.00 |
| Hypoxanthine | 4.10 | — |
| Hypoxanthine (sodium salt) | — | 4.77 |
| Linoleic acid | 0.084 | 0.084 |
| Lipoic acid | 0.21 | 0.21 |
| Phenol red | 1.20 | 1.20 |
| Putrescine 2HCl | 0.161 | 0.161 |
| Sodium pyruvate | 110.00 | 110.00 |
| Thymidine | 0.73 | 0.73 |
| Amino Acids: | | |
| L-Alanine | 8.90 | 8.90 |
| L-Arginine Hcl | 211.00 | 211.00 |
| L-Asparagine.$H_2O$ | 15.01 | 15.01 |
| L-Aspartic acid | 13.30 | 13.30 |
| L-Cysteine | — | — |
| L-Cysteine HC1.$H_2O$ | 35.12 | 35.12 |
| L-Glutamic acid | 14.70 | 14.70 |
| L-Glutamine | 146.00 | 146.00 |
| Glycine | 7.50 | 7.50 |
| L-Histidine HC1.$H_2O$ | 20.96 | 20.96 |
| L-Isoleucine | 3.94 | 3.94 |
| L-Leucine | 13.10 | 13.10 |
| L-Lysine HC1 | 36.50 | 36.50 |
| L-Methionine | 4.48 | 4.48 |
| L-Phenylalanine | 4.96 | 4.96 |
| L-Proline | 34.50 | 34.50 |
| L-Serine | 10.50 | 10.50 |
| L-Threonine | 11.90 | 11.90 |
| L-Tryptophan | 2.04 | 2.04 |
| L-Tyrosine | 5.40 | — |
| L-Tyrosine (disodium salt) | — | 7.78 |
| L-Valine | 11.70 | 11.70 |

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by passing the complete medium containing the marrow cells through syringes fitted with a series of 16, 18, and 20 gauge needles. It is believed that the advantage produced through the utilization of the mechanical separation process, as opposed to any enzymatic separation process, was that the mechanical process produced little cellular change while an enzymatic process could produce cellular damage particularly to the protein binding sites needed for culture adherence and selective separation, and/ or to the protein sites needed for the production of monoclonal antibodies specific for said mesenchymal stem cells. The single cell suspension (which was made up of approximately $50-100 \times 10^6$ nucleated cells) was then subsequently plated in 100 mm dishes for the purpose of selectively separating and/or isolating the mesenchymal stem cells from the remaining cells found in the suspension.

When aspirated marrow was utilized as the source of the human mesenchymal stem cells, the marrow stem cells (which contained little or no bone chips but a great deal of blood) were added to the complete medium and fractionated with Percoll (Sigma, St. Louis, Mo.) gradients more particularly described below in Example 1. The Percoll gradients separated a large percentage of the red blood cells and the mononucleate hematopoietic cells from the low density platelet fraction which contained the marrow-derived mesenchymal stem cells. In this regard, the platelet fraction, which contained approximately $30-50 \times 10^6$ cells was made up of an undetermined amount of platelet cells, $30-50 \times 10^6$ nucleated cells, and only about 50–500 mesenchymal stem cells depending upon the age of the marrow donor. The low density platelet fraction was then plated in the Petri dish for selective separation based upon cell adherence.

In this regard, the marrow cells obtained from either the cancellous bone or iliac aspirate (i.e. the primary cultures) were grown in complete medium and allowed to adhere to the surface of the Petri dishes for one to seven days according to the conditions set forth in Example 1 below. Since no increase in cell attachment was observed after the third day, three days was chosen as the standard length of time at which the non-adherent cells were removed from the cultures by replacing the original complete medium with fresh complete medium. Subsequent medium changes were performed every four days until the culture dishes became confluent which normally required 14–21 days. This represented $10^3-10^4$ fold increase in undifferentiated human mesenchymal stem cells.

The cells were then detached from the culture dishes utilizing a releasing agent such as trypsin with EDTA (ethylene diaminetetra-acetic acid) (0.25% trysin, 1 mM EDTA (1x), Gibco, Grand Island, N.Y.) or a chelating agent such as EGTA (ethylene glycol-bis-(2-amino ethyl ether) N,N'-tetraacetic acid, Sigma Chemical Co., St. Louis, Mo.). The advantage produced through the use of a chelating agent over trypsin was that trypsin could possibly cleave off a number of the binding proteins of the mesenchymal stem cells. Since these binding proteins contain recognition sites, when monoclonal antibodies were sought to be produced, a chelating agent such as EGTA as opposed to trypsin, was utilized as the releasing agent. The releasing agent was then inactivated and the detached cultured undifferentiated mesenchymal stem cells were washed with complete medium for subsequent use.

In this regard, the bone and cartilage lineage potentials (i.e. osteo-chondrogenic potential) of fresh and expanded human mesenchymal stem cells were determined using two different in vivo assays in nude mice. See Example 1 below. One assay involved the subcutaneous implantation of porous calcium phosphate ceramics loaded with cultured mesenchymal stem cells; the other involved peritoneal implantation of diffusion chambers inoculated with cultured mesenchymal stem cells. Whole marrow and Percoll gradient separated aspirate fractions were also analyzed in these in vivo assays. Histological evaluation showed bone formation in the ceramics implanted with the cultured mesenchymal stem cells derived from the femoral head and the iliac crest. No cartilage was observed in any of the ceramic grafts. In contrast, the same cells failed to form any bone or cartilage in the diffusion chambers. While whole marrow has now been shown to form bone when placed as a composite graft with ceramics in a subcutaneous site in nude mice, the amount of bone produced is substantially less than that seen when culture expanded marrow-derived mesenchymal stem cells are used.

These results indicated that under certain conditions, culture expanded mesenchymal stem cells have the ability to differentiate into bone when incubated as a graft in porous calcium phosphate ceramics. Although the internal factors which influence the mesenchymal stem cells to differentiate into bone as opposed to cartilage cells are not well known, it appears that the direct accessibility of the mesenchymal stem cells to growth and nutrient factors supplied by the vasculature in porous calcium phosphate ceramics, as opposed to the diffusion chamber, influenced the differentiation of the mesenchymal stem cells into bone.

As a result, the isolated and culture expanded mesenchymal stem cells can be utilized under certain specific conditions and/or under the influence of certain factors, to differentiate and produce the desired cell phenotype needed for connective tissue repair or regeneration and/or for the implantation of various prosthetic devices. For example, using porous ceramic cubes filled with culture-expanded human mesenchymal stem cells, bone formation inside the pores of the ceramics has been generated after subcutaneous incubations in immunocompatible hosts. In a recent study conducted by the inventor's lab, i.e., Ohgushi, H., Goldberg, V., and Caplan, A. *Acta Scandia.*, 60:334–339, 1989, rat marrow in a composite graft with porous ceramic was used to fill a segmental defect in the femur of the rat. Bone was shown to fill the pores of the ceramic and anchor the ceramic-marrow graft to the host bone.

Production of Monoclonal Antibodies for Human Mesenchymal Stem Cells

The present invention is also directed to the in vitro production of monoclonal antibodies specific to the mesenchymal stem cells which were isolated, purified and culture-expanded as indicated above, and the use of the monoclonal antibodies and associated hybridomas (i.e. the fused myeloma-lymphocyte cells which produce the monoclonal antibodies) for diagnostic and/or therapeutic purposes. The monoclonal antibodies can be utilized not only for identifying, enumerating, localizing, and isolating human mesenchymal stem cells through various diagnostic means such as immunofluorescence, but also for delivering various pharmaceutical products, and additional therapeutic uses.

The mesenchymal stem cells utilized in the invention for immunization were isolated and purified according to the procedure set forth above with the exception that after the first passage of cells that were grown to confluence, the cells were released from the surface of the Petri dish with 0.5 mM EGTA (ethylene glycol-bis-(2-amino ethyl ether) N,N'-tetracetic acid, Sigma Chemical Co., St. Louis, Mo.) in Moscona's Salt Solution (Ca-Mg-free Tyrode's salt solution) for one hour. In this regard, because EGTA acts as a releasing agent possibly through the chelation of $Mg^{+2}$ and $Ca^{+2}$ ions, the mesenchymal stem cells were first soaked with Moscona's (a saline solution containing no $Mg^{+2}$ or $Ca^{+2}$ ions) reagent in order to remove the $Mg^{+2}$ and $Ca^{+2}$ present in the complete medium, and then were incubated in EGTA for one hour. The mesenchymal stem cells were then rinsed with Tyrode's Salts (Catalog No. T-2145, without sodium bicarbonate, Sigma Chemical Co., St. Louis, Mo.), a balanced salt solution which provides certain physiological factors required for the maintenance of the structural integrity of cells in vitro, and reconstituted in Tyrode's salts for injection into a mouse for the production of antibodies.

Along this line, prior to immunization (or stimulation), the mesenchymal stem cells were dissociated into single cells by passage through a 20 gauge needle. A female mouse (CBGF1/J, Jackson Labs, Bar Harbor, Me.) approximately 14 weeks old at the beginning of the immunization process, was immunized with the culture expanded, isolated mesenchymal stem cells by peritoneal injection according to the specific immunization protocol set forth in Example 2. In this regard, since at least one previous attempt failed to produce any monoclonal antibodies specific to the mesenchymal stem cells during immunization, several factors were explored with respect to the optimal immunization procedure in order to produce anti-mesenchymal stem cell secreting hybridomas including (1) cell disassociation (i.e. the cells were dissociated with EGTA and other agents instead of trypsin), (2) the immunizing antigen concentration, (3) the source of the purified mesenchymal stem cells utilized (i.e. cells from several different marrow donors were used to maximize the proportion of common antigens over donor-specific antigens), etc. The procedure which was discovered to produce the optimal results is set forth in detail in Example 2.

Briefly, however, approximately $2.0 \times 10^6$ culture expanded mesenchymal stem cells were initially intraperitoneally injected into the mouse. The initial injection was followed by four booster injections of such stem cells obtained from multiple human donors prepared in a similar fashion spaced approximately a week apart. Cells from multiple donors were utilized for the purposes of producing monoclonal antibodies specific for common epitopes found on the surface of the mesenchymal stem cells. After the 25th day, blood was drawn from the mouse and the serum from the blood was assayed by indirect immunofluorescence in order to check that the immunization regimen had been successful in generating an immune response in the mouse to the cultured mesenchymal stem cells.

After successfully completing the four week immunization process, the mouse was sacrificed and its spleen cells (particularly the antibody-secreting plasma cells, i.e. lymphocytes, producing antibodies with the specificity for the marrow-derived mesenchymal cells) were fused with SP 2/0 myeloma cells (immortal antibody-secreting tumor cells obtained from Dr. Douglas Fambrough at the Carnegie Institute in Baltimore, Md.) according to the very specific fusion procedure set forth below. The SP 2/0 myeloma cells utilized were sensitive to hypoxanthine-aminopterin-thymidine (HAT) medium by virtue of their lacking enzymes such as thymidine kinase (TK). As a result, the SP 2/0 myeloma cells died when exposed to HAT selective medium. This allowed for the selection of hybrids to be accomplished by growing the fused and unfused cells in HAT medium. Moreover, in addition to the SP 2/0 myeloma cells sensitivity to HAT medium, these cells also synthesized no immunoglobulin. The benefit of using a non-immunoglobulin secreting myeloma cell for fusion was that any immunoglobulin associated with the growth of the hybridomas arising from the fusion would indicate only a contribution from the spleen cells.

The process utilized for cell fusion to produce the hybridomas is described in detail in Example 2 below. Generally, however, the spleen cells were first mixed with one-third of the number of the myeloma cells and centrifuged. The cell pellet was then exposed to polyethylene glycol (PEG 1500, Boehringer Mannheim, W. Germany) which promoted cell fusion. The PEG was then subsequently diluted out, and the fusion mixture was centrifuged and the pellet resuspended in specific growth medium (i.e. the HAT medium which killed the myeloma cells while permitting the growth of the hybridomas) with feeder cells (such as mouse peritoneal macrophages which aided in the establishment of hybridomas), plated into aliquots, and incubated according to the feeding and changing schedule set forth in Example 2. After approximately seven to ten days, small clusters or colonies of hybridoma cells (i.e. the immortalized progeny of cell fusion between the tumor cells and the β-lymphocytes found in the mouse spleen) appeared in the wells. Since the myeloma cell line utilized (i.e. SP 2/0 myeloma cells) was a mutant that had lost its ability to produce its own antibodies, the resultant hybridomas secreted only the antibodies of the antibody-secreting plasma cells (β-lymphocytes) obtained from the immunized mouse.

In order to identify those hybridoma colonies which synthesized and secreted antibodies having the specificity for the culture expanded, isolated, and purified human mesenchymal stem cells, a number of preliminary screening techniques (i.e. Enzyme-linked Immunosorbent Assay, Indirect Immunofluorescence Assay, etc.) were utilized to characterize the antibodies which were secreted by the various hybridomas. The positive controls for all assays included sera from the immunized mice at various dilutions obtained at the time of spleen removal.

Specifically, a series of assays were performed in order to identify hybridomas which secreted antibodies with the IgG isotype. Since this isotype was the major secreting antibody and was also the easiest to purify and use, it was preferred over IgM and IgA isotypes which may have also contained the specificity for the desired epitope. As indicated below in Example 2, out of the 764 wells which exhibited hybridoma growth (out of 960 wells initially plated), 245 of these wells tested positive for secreting antibodies with the IgG isotype.

The culture supernatant from colonies which screen positive for the production of IgG antibodies were then screened against frozen sections of pelleted mesenchymal stem cells by indirect immunofluorescence. This assay was performed in order to identify antibodies which bonded only to epitopes on the mesenchymal stem cells. Out of the 245 wells which screened positive for the production of IgG antibodies, only 171 of these wells tested positive for binding with the mesenchymal stem cells.

Since the above screening step was directed to frozen sections of pelleted cultured mesenchymal stem cells, it fails to differentiate those hybridomas which secreted antibodies only specific to the surface of the cell as opposed to the intracellular portion of the cell, the hybridoma supernatants which tested positive in regard to the reactivity for IgG and frozen sections of pelleted cultured mesenchymal stem cells, were then incubated with live cultured human marrow-derived mesenchymal stem cells in micromass cultures (i.e. the cultured cells were replated into small masses located in the center of the tissue culture dishes where the cells remained viable and replicated) and the reactivity was measured by indirect immunofluorescence. Since the cells that were being analyzed were living cells, this assay identified antibodies which bonded to the surface of the cell and gave negative results to antibodies which bonded only to intracellular epitopes. This was important because for the monoclonal antibodies to be utilized as a useful differentiation marker, they needed to be specific to the cell surface.

As indicated below, out of 171 wells which tested positive with reactivity with pelleted cultured mesenchymal stem cells, only 15 of these wells tested positive for reactivity with living cultured mesenchymal stem cells.

The hybridomas which tested positive to each of the above preliminary screens (i.e. 15 out of 960 initial wells) were then cloned by limited dilution to ensure that the subsequent screening was performed on hybridomas which originated only from a single clone. In this regard, since multiple cell lines may have been present in the original "parent" wells (i.e. in the original fusion well, the hybridoma cells may have descended from several fusion products and/or the gradual loss of chromosomes during the initial days after fusion may also have generated additional heterogeneity) cloning of the cells was required to obtain a monoclonal hybridoma cell line. While a detailed description of the cloning process utilized is set forth below in Example 2, the cloning process basically involved the steps of replating the cells present in the original parent wells at a density of less than one cell per well. As a result of the establishment of the single cell cultures, any colony which grew in the wells was the progeny of only the original replated cells. In order to assure monoclonality, multiple clonings were performed until 100% of the subclones were positive for two generations.

The cell lines or clones were then propogated in tissue cultures or in vivo in syngeneic or immunocompatible hosts where they continued to synthesize and secret antibodies to the purified marrow-derived mesenchymal stem cells. These antibodies were then recovered from the tissue culture cells or the ascites fluid by conventional techniques such as precipitation, ion exchange, affinity chromatography, etc.

The cloned hybridomas were then subsequently screened against a series of mesenchymal and non-mesenchymal derived tissues in order to identify the degree of specificity of the monoclonal antibodies to the cultured mesenchymal stem cells. Specifically, in order to determine that the monoclonal antibodies were not specific (i.e. did not react) to the hematopoietic lineage cells in marrow (and thus could be utilized to differentiate mesenchymal stem cells from the hematopoietic cells), whole marrow and several partial fractionations of the marrow were screened against hybridoma culture supernatant by indirect immunofluorescence. The results are set forth below in Table 5 (see Example 2).

In addition, in order to determine if the monoclonal antibodies reacted to epitopes common to mesenchymal stem cells and differentiated mesenchymal tissues, frozen sections of a variety of mesenchymal tissues that were obtained at surgery or autopsy were screened against the hybridoma culture supernatant by indirect immunofluorescence. The positive and negative reactivities were noted and are set forth in Table 5.

Furthermore, in order to identify hybridomas which secreted antibodies which were only specific for mesenchymal stem cells and/or their lineage descendants (i.e. antibodies which failed to react to non-mesenchymal derived tissue), the hybridoma culture supernatants were incubated with sections of non-mesenchymal derived tissue and the antibody reactivity was analyzed by indirect immunofluorescence. The results are also set forth in Table 5 below.

An analysis of the data indicated that three of the hybridomas produced, identified, and cloned by the present invention (i.e. SH2, SH3, and SH4) were useful for the analysis of mesenchymal stem cells. All three of these hybridomas secreted antibodies which reacted to cell surface epitopes on 99–100 of cells in the assays of the culture-expanded mesenchymal stem cells. In contrast, each of the three hybridomas secreted antibodies which reacted to less than 1% of the cells in assays of whole marrow. The ability of these antibodies to selectively bind mesenchymal stem cells and not hematopoietic cells make them excellent probes for quantitating the number of mesenchymal stem cells in samples and for purifying mesenchymal stem cells.

In addition, all three of the hybridomas showed mostly negative cross reactivity when screened against a variety of mesenchymal and non-mesenchymal derived tissues, although some cross reactivity was observed with each. Of particular interest, SH3 and SH4 cross reacted to cell surface determinants on cultured cells derived from human periosteum. In this regard, the inventors previously demonstrated that periosteum was another source of mesenchymal stem cells and the cross reactivity of the above antibodies to cell surface epitopes on periosteal cells suggested a structural relationship between the marrow-derived mesenchymal stem cells and periosteum-derived mesenchymal stem cells. The SH2 antibody has now been found to also react to periosteum-derived mesenchymal stem cells as well as to marrow-derived mesenchymal stem cells.

Deposits of the cell line cultures identified as SH2, SH3, and SH4 are on deposit with the American Type Culture Collection, 12301 Parklawn Drive, Rockville, Md., 20852, and are assigned the ATCC accession numbers HB 10743, HB 10744, and HB 10745, respectively. The deposits are for the purpose of enabling disclosure only and are not intended to limit the concept of the present invention to the particular materials deposited.

The results indicated that the generated monoclonal antibodies recognized cell surface determinants on the mesenchymal stem cells but not certain other cells such as hematopoietic cells, etc. Since there were previously no specific markers for marrow-derived or periosteum-derived mesenchymal stem cells, the generated monoclonal antibodies now provide for effective mono-specific probes which can be utilized for identifying, quantifying, and purifying mesenchymal stem cells, regardless of their source in the body.

More particularly, the monoclonal antibodies produced can be labelled with suitable radioactive, enzymatic, or fluorescent labels by conventional methods and/or bound to suitable solid carriers, which will be apparent to those skilled in the art. In this regard, Example 3 below demonstrates the effectiveness of the generated monoclonal antibodies for identifying and/or quantifying the presence of marrow-derived mesenchymal stem cells in biological samples such as bone marrow with conventional immunological methods. For example, the monoclonal antibodies can be used in combination with, or coupled to, an immunochemical such as fluorescein isothiocyanate, peroxidase, biotin and its analogs (e.g., iminobiotin), avidin and its analogs (streptavidin), alkaline phosphatases, or other such markers. Moreover, the monoclonal antibodies can be bound or attached to certain substrates and utilized to capture mesenchymal stem cells when tissue samples such as bone marrow are brought in contact with the attached monoclonal antibodies. The bound cells may then be separated from the solid phase by known methods depending essentially upon the nature of the solid phase and the antibody. The unbound cells can be recovered and used for various therapeutic purposes such as for the regeneration of bone, etc., depending upon the various external and internal factors.

As a result, the present invention contemplates any method of employing monoclonal antibodies to separate mesenchymal stem cells from other cells such as hematopoietic cells. For example, a further embodiment of the present invention is directed to a method of producing a population of mesenchymal stem cells comprising the steps of providing a cell suspension of tissue containing mesenchymal cells; contacting the cell suspension with monoclonal antibodies which recognize an epitope on the mesenchymal stem cells but do not recognize an epitope on the hematopoietic cells or any other bone marrow cells; and separating and recovering from the cell suspension the cells bound by the monoclonal antibodies.

In addition, an alternate embodiment of the invention is directed to a method of providing a population of mesenchymal stem cells comprising the steps of providing a cell suspension of tissue containing mesenchymal cells; contacting the cell suspension with solid-phase linked monoclonal antibodies which recognize an epitope present on the cell surface of the mesenchymal stem cells but not on hematopoietic cells; separating the unbound cells from the solid-phase linked monoclonal antibodies; and, recovering the bound cells from the liquid linked monoclonal antibodies.

Compositions according to the present invention which contain mesenchymal stem cells are especially useful for facilitating repair, reconstruction and/or regeneration of a connective tissue defect. Connective tissue, as used herein, includes bone, cartilage, ligament, tendon, stroma and muscle. Connective tissue defects include any damage or irregularity compared to normal connective tissue which may occur due to trauma, disease, age, birth defect, surgical intervention, etc. As used herein, connective tissue defects also refer to non-damaged areas in which cosmetic augmentation is solely desired. The methods and materials disclosed herein are especially suitable for use in orthopedic, dental, oral maxillofacial, periodontal, and other surgical procedures.

Although in a preferred embodiment, the mesenchymal stem cells are culturally expanded prior to use, it is also possible to use such mesenchymal stem cells without culture expansion. For example, mesenchymal stem cells may be derived from bone marrow and used after separation of blood cells therefrom, without expansion. Thus, for example, during a surgical procedure for repairing connective tissue using mesenchymal stem cells, bone marrow may be obtained from a patient, enriched in human mesenchymal stem cells, by removal of blood cells and reintroduced to the patient during the procedure. The marrow-derived cells containing mesenchymal stem cells which are essentially free of blood cells may then be used to repair the patient's connective tissue.

Various vehicles may be employed for delivery of human mesenchymal stem cells for repair of connective tissue. The compositions may be designed as a patch for the damaged tissue to provide bulk and scaffolding for new bone or cartilage formation. The various compositions, methods, and materials described herein can, in accordance with the present invention, be used to stimulate repair of fresh fractures, non-union fractures and to promote spinal fusion. Likewise, repair of cartilage and other musculoskeletal tissues can be accomplished. In the case of spinal fusion, such compositions, methods, and materials can be used posteriorly with or without instrumentation to promote mass fusion along the lamina and transverse processes and anteriorly, used to fill a fusion cage to promote interbody fusion.

The following examples are included for the purposes of further illustrating the detailed steps of the present invention.

EXAMPLE 1

The Isolation, Purification and Culture Expansion of Human Mesenchymal Stem Cells Marrow Harvest Marrow in femoral head cancellous bone pieces was obtained from patients with degenerative joint disease during hip or knee joint replacement surgery. In addition, marrow was also obtained by iliac aspirate from normal donors and oncology patients who were having marrow harvested for future bone marrow transplantation. All of the oncology patients had malignancies unrelated to the stromal cells and the stromal cells expressed normal karyotype.

Preparation of Marrow for Cell Culture

A. From Plugs of Cancellous Bone Marrow

Plugs of cancellous bone marrow (0.5–1.5 ml) were transferred to sterile tubes to which 25 ml $BGJ_b$ medium (GIBCO, Grand Island, N.Y.) with selected batches of 10% fetal bovine serum (JR Scientific, Woodland, Calif.) (complete medium) was added. The tubes were vortexed to disperse the marrow then spun at 1000×RPM for 5 minutes to pellet cells and bone pieces. The supernatant and fat layer were removed and the marrow and bone were reconstituted in 5 ml complete medium and vortexed to suspend the marrow cells. The suspended cells were collected with a 10 ml syringe fitted with a 16 gauge needle and transferred to separate tubes. Bone pieces were reconstituted in 5 ml. complete medium and the marrow cells were collected as before. Collection of marrow cells was considered complete when a pellet of yellowish-white cancellous bone pieces was all that remained in the original tube. Marrow cells were separated into a single cell suspension by passing them through syringes fitted with 18 and 20 gauge needles. Cells were spun at 1000×RPM for 5 minutes after which the fat layer and supernatant were removed. Cells were reconstituted in complete medium, counted with a hemocytometer (red blood cells were lysed prior to counting with 4% acetic acid), and plated in 100 mm dishes at 50–100×10$^6$ nucleated cells/dish.

As indicated above, the complete medium can be utilized in a number of different isolation processes depending upon the specific type of initial harvesting processes used in order to prepare the harvested bone marrow for cell culture separation. In this regard, when plugs of cancellous bone marrow were utilized, the marrow was added to the complete medium and vortexed to form a dispersion which was then centrifuged to separate the marrow cells from bone pieces, etc. The marrow cells (consisting predominantly of red and white blood cells, and a very minute amount of mesenchymal stem cells, etc.) were then dissociated into single cells by passing the complete medium containing the marrow cells through syringes fitted with a series of 16, 18, and 20 gauge needles. The advantage produced through the use of the mechanical separation process, as opposed to any enzymatic separation process, was that the mechanical process produced little cellular change while an enzymatic process could produce cellular damage particularly to the protein binding sites needed for culture adherence and selective separation, and/or to the protein sites needed for the production of monoclonal antibodies specific for the mesenchymal stem cells. The single cell suspension (which was made up of approximately 50–100×10$^6$ nucleated cells) was then subsequently plated in 100 mm dishes for the purpose of selectively separating and/or isolating the marrow-derived mesenchymal cells from the remaining cells in the suspension.

B. From Aspirate Bone Marrow

Aspirate marrow (5–10 ml) was transferred to sterile tubes to which 20 ml complete medium was added. The tubes were spun at 1000×RPM for 5 minutes to pellet the cells. The supernatant and fat layer were removed and the cell pellets (2.5–5.0 ml) were loaded onto 70% Percoll (Sigma, St. Louis, Mo.) gradients and spun at 460×g for 15 minutes. The gradients were separated into three fractions with a pipet: top 25% of the gradient (low density cells—platelet fraction), pooled density=1.03 g/ml; middle 50% of the gradient (high density cells-mononucleated cells), pooled density=1.10 g/ml; and, bottom 25% of the gradient (red blood cells), pooled density=1.14 g/ml. In preliminary experiments each of these three pools were plated separately in complete medium in 100 mm dishes. Adherent cells were observed to be localized to the low density cells. To produce adherent cell cultures for all subsequent experiments, only the low density cells were plated.

Culturing and Passaging of Marrow Stromal Cells

Marrow cells from either the femoral head cancellous bone or the iliac aspirate were cultured in complete medium (i.e. BGI$_b$ medium with 10% fetal bovine serum) at 37° C. in humidified atmosphere containing 95% air and 5% $CO_2$.

In preliminary experiments the cells were allowed to attach for 1, 3, or 7 days prior to the initial medium change. No increase in cell attachment was observed after day 1, therefore, one day was chosen as the standard length of time at which nonadherent cells were removed from the cultures by replacing the original medium with 7 ml of fresh complete medium. Subsequent medium changes were performed every 4 days. When culture dishes became confluent, the cells were detached with 0.25% trypsin with 0.1 mM EDTA (GIBCO) for 10–15 minutes at 37° C. The action of trypsin was stopped with ½ volume fetal bovine serum. The cells were counted, split 1:3, and replated in 7 ml complete medium. Aliquots of cells were cryopreserved in 90% fetal bovine serum with 10% DMSO (freezing medium).

Preparation of Cultures for In Vivo Incubations in Ceramics and Diffusion Chambers Cultured cells were detached from plates as described for subculturing. After inactivating the trypsin, the cells were washed twice with 10 ml serumless BGJ$_b$ medium, counted, and then adjusted to the appropriate concentration with serumless BGJ$_b$. Whole marrow and Percoll fractions were rinsed twice with 10 ml serumless BGJ$_b$ and adjusted to the appropriate concentration with serumless BGJ$_b$. Porous ceramic cubes (3 mm$^3$) composed of 60% hydroxyapatite+40% β-tricalcium phosphate (Zimmer Corporation, Warsaw, Ind.) were added to the cell suspensions under slight vacuum and soaked for up to 90 minutes prior to surgical implantation.

Diffusion chambers were constructed of lucite rings and Millipore filters as described elsewhere (Ashton, et al., 1980). Cells were prepared as described above and added to the chambers in 100–140 μl of serumless BGJ$_b$ medium. Chambers were sealed with a drop of cement and immersed in serumless BGJ$_b$ for up to 90 minutes prior to surgical implantation.

Surgical Implantation of Ceramics and Diffusion Chambers

Ceramics—Nude mice (National Institute of Health, nu/nu strain) were anesthetized with ether and placed on their stomachs. Four small longitudinal incisions (5 mm) were made along the backs. Ceramic-marrow grafts were inserted into the pockets and positioned as lateral in the pockets as possible. Incisions were closed with Autoclips (Becton Dickinson and Company, Parsippany, N.J.). Each pair of pockets received a different pair of ceramic-marrow graft so that four different samples (2 ceramic cubes per sample) were incubated per mouse.

Diffusion Chambers—Nude mice were anesthetized with ether and placed on their backs. Incisions were made through the skin and peritoneum, and diffusion chambers were inserted into the peritoneal cavity. The peritonea were closed with sutures and the skin, with Autoclips. Only one chamber was inserted per mouse and it contained cultured cells identical to cells loaded in one of the four pairs of the ceramic-marrow grafts implanted into the same mouse.

Histological Evaluation

Nude mice were sacrificed and the ceramic-marrow grafts harvested 1–8 weeks after implantation (Table 1 and Table 3). Grafts were fixed in 10% buffered formalin, demineralized fr 7 hours in RDO Rapid Bone Decalcifier (Dupage Kinetics Laboratories, Inc., Plainfield, Ill.), embedded in paraffin, serial sectioned (5 μm thick), and stained with Mallory Heidenhain or Toluidine blue.

Diffusion chambers were harvested 3–10 weeks after implantation (Table 2 and Table 3). Chambers were fixed in 10% buffered formalin, paraffin embedded, serially sectioned, and stained with Mallory Heidenhain or Toluidine blue.

TABLE 1

Incubation of Composite Grafts of Cultured Human MSCs and Ceramic Matrix in Nude Mice

| Donor # | Age/Sex | Site | Pass # | Conc. | Weeks Postimplantation | | | | | | | |
|---|---|---|---|---|---|---|---|---|---|---|---|---|
| | | | | | 1 | 2 | 3 | 4 | 5 | 6 | 7 | 8 |
| 1 | 50/M | FH | 4 | $20 \times 10^6$ | | | | | − | + | | |
| 1 | 50/M | FH | 5 | $2 \times 10^6$ | | − | | | + | + | | |
| 1 | 50/M | FH | 6 | $0.7 \times 10^6$ | | + | + | | | | | + |
| 2 | 65/M | FH | 1 | $5 \times 10^6$ | | | | | ++ | +++ | | |
| 2 | 65/M | FH | 2 | $4 \times 10^6$ | | | +++ | | | +++ | | +++ |
| 3 | 65/M | FH | P | $6 \times 10^6$ | − | + | | | | +++ | +++ | +++ |
| 4 | 66/F | FH | 1 | $10 \times 10^6$ | | + | | | ++ ++ | +++ | | +++ |
| 5 | 64/M | FH | P | $8 \times 10^6$ | − | + | ++ | | | +++ | | +++ |
| 6 | 64/M | FH | 1 | $4 \times 10^6$ | | + | | | | +++ | | +++ |
| 7 | 67/F | FH | P | $7 \times 10^6$ | − | + | ++ | +++ | | | | |
| 8 | 34/F | IC | 1 | $4 \times 10^6$ | | | − | | | + | | |
| 9 | 42/M | IC | P | $4 \times 10^6$ | | | − | | | − | | |
| 10 | 38/M | IC | P | $4 \times 10^6$ | | | − | | | ++ | | |
| 11 | 45/M | IC | P | $4 \times 10^6$ | | | + | | | ++ | | |

Pass # is the number of subcultures
Conc. is the concentration of cells in cells/ml
Site is the site of marrow harvest
FH - femoral head
IC - Iliac crest
P - primary cultures
− = None of the pores contained bone
+ = 0–30% of the pores contained bone
++ = 30–70% of the pores contained bone
+++ = greater than 70% of the pores contained bone

TABLE 2

Incubation of Cultured Human Marrow-Derived Mesenchymal Stem Cells in Diffusion Chambers

| Donor | Age/Sex | Site | Pass # | Cells/Chamber | 3 | 6 | 8 | 10 |
|---|---|---|---|---|---|---|---|---|
| 1 | 50/M | FH | 4 | $4 \times 10^6$ | | − | | |
| 2 | 65/M | FH | 1 | $3 \times 10^6$ | | − | | |
| 3 | 65/F | FH | P | $4 \times 10^6$ | | − | − | |
| 4 | 66/F | FH | 1 | $4 \times 10^6$ | − | | | − |
| 5 | 64/M | FH | P | $4.5 \times 10^6$ | | − | | |

P = primary culture
Pass # = the number of subcultures
Site = the site of marrow harvest
FH = femoral head
IC = iliac crest
− = no bone in chamber
+ = 0–30% of chamber contains bone
++ = 30–70% of chamber contains bone
+++ = more than 70% of chamber contains bone

RESULTS

In Vitro Cultures

Adherent mesenchymal stem cells from femoral head cancellous bone or iliac aspirate have similar morphology, almost all being fibroblastic, with few adipocytic, polygonal or round cells (FIG. 1). Histochemical staining for alkaline phosphatase yields variable positive reactivity with no noticeable difference between cells derived from cancellous bone marrow or aspirate marrow. Adherent cells from both harvest sites fail to produce an extracellular matrix which stains metachromatically with Toluidine blue or positive for von Kossa; a positive staining would have indicated the possibility that cartilage or bone tissue was produced in these cultures.

In Vivo Incubation of Cultured Marrow Cells with Ceramics

Calcium phosphate ceramic blocks were soaked in culture medium containing various concentrations of cultured marrow-derived mesenchymal stem cells from either femoral head cancellous bone or iliac aspirate. The marrow donors included both males and females ranging in age from 34 to 67 years old (Table 1). Cells from primary culture and first through sixth passage were assayed, with the cell-loading concentration ranging from $0.7 \times 10^6$ to $20 \times 10^6$ cells/ml. Marrow-derived mesenchymal stem cell-loaded ceramic blocks were surgically implanted subcutaneously into nude mice and incubated from 1 to 8 weeks. Upon harvest, ceramics were fixed, demineralized and the presence of bone and cartilage was determined by histological evaluation. Table 1 summarizes the data.

Bone, but not cartilage, was observed in the pores of each graft of ceramics and cultured marrow-derived mesenchymal stem cells from femoral head cancellous bone. The earliest bone was observed at 2 weeks in less than 30% of the pores of each ceramic (FIG. 2). At three weeks, the number of pores containing bone varied from less than 30% to greater than 70% (FIG. 3). By six weeks, the majority of the ceramics contained bone in greater than 70% of the pores (FIG. 4). No obvious correlation could be made between the age of the donors and the amount of bone formation. In contrast, passage number appeared to have some influence on the amount of bone formation, with primary cultures and early passaged cells (1st–2nd passages) giving more bone formation than late passaged cells (4th–6th passages). Bone formation appears to begin with osteoblast differentiation and bone deposition onto the surfaces of the ceramic pores and appears to progress towards the center of the pores as cells lining the surface of the new bone matrix secrete osteoid on top of previously deposited matrix. Maintenance of ceramic mesenchymal stem cell grafts for periods of 6–8 weeks resulted in bone remodeling and the identification of marrow elements in the inner spaces of each pore (FIG. 2C).

Grafts of ceramics and cultured mesenchymal stem cells from iliac aspirate produced bone in three of the four samples tested (Table 1). Cartilage was not observed in any of the grafts. Bone formation in the three positive grafts was less than that observed from ceramics grafted with cultured cells from femoral head cancellous bone marrow. Less than 30% of the pores contained bone at 3 weeks and 30–70% of the pores contained bone at 6 weeks. The remainder of the pores contained fibrous tissue and vasculature of, in all likelihood, host origin.

In Vivo Incubation of Cultured Marrow Cells in Diffusion Chambers

The osteo-chondrogenic potential of cultured marrow-derived mesenchymal stem cells was also assayed by loading cells in diffusion chambers and surgically implanting them intraperitoneally into nude mice. The cells were obtained from the same cultures used in the ceramic assays (Table 2), and the diffusion chambers were implanted into the peritonea of the same nude mice which received subcutaneous ceramic-marrow-derived mesenchymal stem cell grafts. After incubations for 3–10 weeks, the chambers were harvested and the presence of bone and cartilage formation determined by histological evaluation. In contrast to the presence of bone in grafts of ceramic and cultured cells from cancellous bone, no bone or cartilage was observed in any of the diffusion chambers containing cultured cancellous bone marrow-derived mesenchymal stem cells even after 10 weeks incubation (Table 2). Cultured iliac aspirate marrow-derived mesenchymal stem cells also failed to produce bone or cartilage in the diffusion chambers. Instead, hypocellular sparse fibrous tissue was observed in most of the chambers.

Discussion

In this example, human marrow-derived mesenchymal stem cells were shown to reproducibly exhibit osteogenic potential following their mitotic expansion in culture when assayed in porous calcium phosphate ceramics in nude mice. Osteogenesis was not observed when the same cells were incubated in diffusion chambers in the same nude mice. Collectively, these data show that human marrow contains mesenchymal stem cells, which can be selected and expanded in culture, which have the potential to differentiate into bone when incubated in vivo as a graft in porous calcium phosphate ceramics.

The absence of bone formation in diffusion chambers suggests that the ceramic assay may be a more sensitive assay for differentiation of bone from marrow cells. Bab, et al. (Bab, I., Passi-Even, L., Gazit, D., Sekeles, E., Ashton, B. A., Peylan-Ramu, N., Ziv, I., and Ulmansky, M.; Osteogenesis in in vivo diffusion chamber cultures of human marrow cells, *Bone and Mineral*, 4:373, 1988) observed bone in four of eight diffusion chambers implanted with human marrow from two child donors; however, these authors failed to observe bone when whole marrow from older donors was incubated in diffusion chambers in nude mice. In addition, Davies (Davies, J. E., Human bone marrow cells synthesize collagen, in diffusion chambers, implanted into the normal rat, *Cell. Biol. Int. Rep.* 11(2):125, 1987) did not observe bone formation in diffusion chambers inoculated with fresh marrow from a five year old female, nor was bone formation observed by Ashton, et al. (Ashton, B. A., Cave, F. A., Williamson, M., Sykes, B. C., Couch, M., and Poser, J. W.; Characterization of cells with high alkaline phosphatase activity derived from human bone and marrow; preliminary assessment of their osteogenicity, Bone, 5:313–319, 1985) in diffusion chambers inoculated with cultured fibroblasts from composite pieces of bone and marrow from children and young adults.

In the present example, bone formation was not observed in diffusion chambers inoculated with cultured marrow-derived mesenchymal stem cells from several older donors. However, bone formation was observed in ceramic filled grafts with cultured marrow-derived mesenchymal stem cells from the same preparations of older donors (34–67 years old) which failed to generate bone in diffusion chambers. The factors which apparently make ceramics a more sensitive vehicle than the diffusion chambers for bone differentiation from marrow-derived mesenchymal stem cells are believed to involve direct accessibility of the mesenchymal stem cells to growth and nutrient factors supplied by the vasculature or direct interaction with vascular cells which are limited because of diffusion chamber geometry (Jaroma, H. J., and Rotsila, V. A., Effect of diffusion chamber pore size on differentiation and proliferation of periosteal cells, *Clin. Orthop.*, 236:258, 1988) (Villanueva, J. E., and Nimni, M. E., Promotion of calvarial cell osteogenesis by endothelial cells in diffusion chambers, *J. Cell. Biol.*, 109, 4, part. 2:42a (abstract).

The question of origin of the bone formed in the ceramic pores is important since the donor marrow-derived mesenchymal stem cells are not physically separated from the host cells as is the case for diffusion chambers. Recent data by Goshima et al. (Jun Goshima, Victor M. Goldberg and Arnold I. Caplan, "The Origin of Bone Formed in Composite Grafts of Porous Calcium Phosphate Ceramic and Marrow Cells", (1989) indicate that bone formation in ceramic grafts is a biphasic phenomenon with the initial bone formation being of donor origin. When this donor-derived bone has partially filled the pores of the ceramics, host-derived cells begin remodeling the donor bone, thus beginning the second phase of host-derived bone formation. Eventually, a marrow cavity forms in the center, with a cocoon of host-derived bone which has been laid on the partially remodeled inner surfaces of original donor bone. To confirm the origin of the bone formed with human marrow, the present inventors are currently assaying ceramic grafts with species-specific monoclonal antibodies directed against human osteocytes. The preliminary data show antibody reactivity to the osteocytes within the grafts, suggesting that the bone formed in the porous ceramic is of human and not mouse origin.

Cultured marrow-derived mesenchymal stem cells originating from femoral head cancellous bone appear to be more osteogenic than cultured marrow-derived mesenchymal stem cells from iliac aspirated marrow; 9 out of 9 cancellous bone marrow samples produced bone in ceramics, whereas, 3 out of 4 aspirated marrow-derived mesenchymal stem cell samples produced bone in ceramics. In addition, bone was present in fewer pores in ceramics grafted with aspirated marrow-derived mesenchymal stem cells than ceramics grafted with femoral head marrow-derived mesenchymal stem cells. The reasons for the differences may be associated with the proximity of the harvested marrow stromal cells to the bone surface in the original tissue. Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.*, 36:83, 1984) showed that cultured rabbit marrow stromal cells differ in their colony forming potential in vitro and osteogenic potential in diffusion chambers depending on their original proximity to the endosteal surface. Cells closest to the endosteal surface were shown to have four times the colony forming efficiency as compared to cells of the core. In the present study, marrow from cancellous bone was harvested by vigorous vortexing to separate the cancellous bone from the marrow cells. This likely produces a population of marrow enriched in cells derived from near the endosteal surface, as compared to aspirate marrow where vigorous separation of marrow cells from cancellous bone is not possible. The inventors observed a consistently higher initial number of adherent cells from cancellous bone marrow as compared to aspirate marrow, which is similar to the observations of Ashton, et al. (Ashton, B. A., Eaglesom, C. C., Bab, I., and Owen, M. E., Distribution of fibroblastic colony-forming cells in rabbit bone marrow and assay of their osteogenic potential by an in vivo diffusion chamber method, *Calcif. Tissue Int.*, 36:83, 1984).

In the case of marrow from adult donors, cartilage was not observed in this study or the study by Bab, et al. (Bab, I., Passi-Even L., Gazit, D., Sekeles, E., Ashton, B. A., Peylan-Ramu, N., Ziv, I., and Ulmansky, M.; Osteogenesis in in vivo diffusion chamber cultures of human marrow cells, *Bone and Mineral* 4:373, 1988). It may be that there is an age-dependent determination of marrow-derived cells for the osteogenic lineage over the chondrogenic lineage. Alternatively, culturing conditions in the present study may be selective for osteoprogenitor cells over mesenchymal stem cells or may drive mesenchymal stem cells towards the osteogenic lineage prior to in vivo analysis in ceramics. Present studies are being directed towards addressing these possibilities.

The most important realization from the studies set forth in the above example is that the ceramic graft technique provides a sensitive assay for identifying the osteogenic potential of marrow-derived mesenchymal stem cells. Importantly, such osteogenic cells can be obtained from human donors of a wide age range. These observations indicate that the ex vivo expansion of cells possessing an osteogenic potential may be used for clinical circumstances requiring augmentation of osteogenesis.

Furthermore, the marrow-derived mesenchymal stem cells isolated and utilized above are characterized by having cell surface antigens that are uniquely recognized by the monoclonal antibodies of the invention. As more clearly indicated below, the hybridoma cell lines and respective monoclonal antibodies are referred to as SH2, SH3, SH4 (ATCC Accession Nos. HB10743, HB10744, and HB10745), respectively.

EXAMPLE 2

Production of Cloned Hybridomas to Human MSCs

I. Immunization

A female mouse (CB6F/J Jackson Labs, Bar Harbor, Me.), approximately 14 weeks old at the beginning of the experiment, was immunized by peritoneal injections with cultured human marrow-derived mesenchymal stem cells obtained from multiple donors (see Table 3 below). The initial injection was followed by four booster injections spaced one week apart. Marrow cells from multiple donors were utilized for the purposes of producing monoclonal antibodies specific for common recognition sites on the mesenchymal stem cells.

TABLE 3

Background Information on Marrow Donors Used in Mouse Immunization

| Prep. # | Date Obtained | Birth date | Type of Prep. | Clinical Diagnosis |
| --- | --- | --- | --- | --- |
| H-20 | 12/16/88 | 04/09/37 | Plug | DJD |
| H-21 | 01/05/89 | 01/01/38 | Plug | DJD |
| H-23 | 01/12/69 | 02/23/09 | Plug | DJD |
| H-27 | 01/17/89 | 12/12/25 | Plug | DJD |
| H-31 | 01/19/89 | Approx. 1929 | Plug | DJD |

Plug = a plug of cancellous bone and marrow which is scooped out of discarded femoral heads during hip transplant surgery
DJD = Degenerative joint disease The Immunization Schedule A. Day 0—The initial injection consisted of cells from donor H-20 which were isolated and purified according to the procedure set forth above in Example 1. Cells from primary cultures were grown to confluence and replated (1:3). These first passaged cells were also grown to confluence and then released from the plate with 0.5 mM EGTA in Moscona for one hour. The cells were rinsed twice with Tyrode's and then reconstituted in 500 $\mu$l Tyrode's for injection into the mouse. The cells were dissociated to single cells by passing through a 20 gauge needle fitted on a one ml syringe and then injected into the peritoneal cavity of the mouse. Approximately $2.0 \times 10^6$ cells were used. All subsequent booster injections were prepared in a similar fashion.

B. Day 7—Cells were derived from donors H-21 and H-23 and collected after confluence of the primary cultures. Approximately equal numbers from each donor was used with the total cell count=$1.5 \times 10^6$.

C. Day 15—Cells were derived from donor H-27 after primary culture. Total cell count=$1.0 \times 10^6$.

D. Day 22—Cells were derived from donor H-31 at confluence after the first passage. Total cell count=$1.0 \times 10^6$.

E. Day 29—Cells were derived from donor H-31. Cells were harvested at confluence after the first passage and cryopreserved in liquid nitrogen. Immediately prior to injection, cells were thawed and prepared and injected as described above on Day 0. Total cell count=$2.0 \times 10^6$.

At day 25 blood was drawn from the tail vein of the mouse and serum was prepared by spinning out the blood cells. The serum was incubated to a frozen section of pelleted cultured human marrow cells and assayed by indirect immunofluorescence. The serum reacted positively to the cells in the frozen section, indicating that the immunization regimen had been successful in generating an immune response in the mouse to the cultured cells.

II. Fusion

After successfully completing the four week immunization process, the immunized mouse was sacrificed and its spleen cells were fused with SP 2/0 myeloma cells obtained from Dr. Douglas Fambrough at the Carnegie Institute in Baltimore, Md., according to the specific process set forth below. However, in order to provide conditioned medium for the hybridoma cells produced during the fusion process, it was necessary to prepare at least a day prior to fusion a "feeder layer" comprised of conditioned medium and peritoneal macrophages. The peritoneal macrophages were added in order to clean the culture dishes through phagocytic action. The following procedures were utilized to produce the feeder layer and to prepare the SP 2/0 myeloma cells for fusion.

A. Preparation of Feeder Cells

Since lymphoid cells often grow poorly or die when grown at low density (the reasons for this are not well understood, but may relate to the requirements for "growth factors" or to the problems of toxic by-products of the tissue culture vessel), the addition of a slow-growing or non-growing population of cells (usually termed "feeders") was necessary. The feeder cells utilized in the current process were produced according to the following procedure.

1. 0.34M (11–64 g/100 ml) sucrose solution was filtered for sterilization and the solution was stored in 15 ml aliquots at 4° C.

2. A mouse was sacrificed by cervical dislocation and immersed completely in 70% EtOH. After several minutes in EtOH, the mouse was removed and laid supine on a styrofoam test tube rack.

3. A midline cut was made in the abdominal skin. Using blunt dissection, the skin was spread away from the peritoneum making sure not to puncture the thin membrane.

4. Using a 20 gauge needle, 5 ml of sucrose was injected into the peritoneum.

5. The needle was removed and the abdomen was gently massaged in order to liberate the macrophages. A 23 gauge needle was inserted into the abdomen and the 5 ml of sucrose was slowly recovered.

6. Steps 4 and 5 were repeated two times and the macrophages were pooled.

7. At 1000 rpm (200 g) the cells were spun for 5 minutes on a Sorvall GLC-4 with an H1000 rotor (r=18.6 cm). The cell pellet was resuspended in 15 ml D-MEM (Dulbecco's Modified Eagle's Medium, Gibco, Grand Island, N.Y., #430–2100)/10% FBS (Fetal Bovine Serum, Gibco, #430, 2100) and spun.

8. The pellet was brought up in 2 ml of medium and the cells counted. An average yield was 3 to 6 million cells.

9. The cells were resuspended in Super HAT medium at a concentration of $1 \times 10^5$ cells/ml. In this regard, Super HAT medium consisted of 400 ml D-MEM, 120 ml FBS, 60 ml NCTC-109-Hybridoma Growth Supplement (M.A. Bioproducts #12-923A), 12 ml 50×HAT or H+T (Boehringer Mannheim #644579 or #623091, respectively), 6 ml Solution I (supplemented D-MEM to provide proper pH and enhanced growth of the hybridomas, contained 0.2 units/ml Insulin, 0.5 mM Na Pyruvate, and 1.0 mM oxaloacetic Acid), 6 ml L-Glutamine (Gibco #320-5030), 0.6 ml Gentamicin (M.A. Bioproducts #17-5182).

10. 0.1 ml of the suspension was then added to each well of ten 96-well culture dishes. Ten dishes were used per fusion.

11. The wells were stored in a 37° C. humid incubator with 5% carbon dioxide, 95% air.

B. Preparation of SP 2/0 Myeloma Cells

The myeloma cells obtained from Dr. Fambrough were evaluated in order to ensure that they were growing well in culture for not less than 2 months prior to the fusion procedure. The cells were passed in DMEM (Dulbecco's Modified Minimal Eagle's medium)/10% FBS/8-Azaguanine (Gibco, Grand Island, N.Y.) in order to select for HAT sensitive cells. Passage of either myeloma or hybridoma cells was accomplished by serially diluting an aliquot across 12 wells of a 48-well plate.

Two weeks prior to fusion, the medium was step-wise adjusted up to 20% FBS. One week prior to fusion, several large flasks (75 cm$^2$, 20 ml of medium) of SP 2/0 myeloma cells were initiated. At that time two rows of a 24-well plate were seeded with SP 2/0 myeloma cells at low density. One day later, the medium was then changed in one of the rows with the same Super HAT medium which was going to be used for fusion. (Prior to using any medium, a sample from each bottle was tested for sterility and bacterial growth). Within 24 hours, most of the cells fed HAT were dead, and by 72 hours, all cells fed HAT (hypoxanthine, aminopterin, thymidine) were dead. Cells fed SP 2/0 growth medium remained healthy.

Two days before the fusion, the SP 2/0 myeloma cells were split into three new flasks at various dilutions (i.e. 1:20, 1:10, 1:8, 1:4). The cells were carefully monitored at various dilutions and only those cells which were in log phase of growth were selected for fusion. There were no dead or dying cells in the selected population. A flask containing the good density of log phase cells contained a total of one to ten million cells.

C. The Fusion Procedure

Materials—per spleen

Dissecting scissors, large forceps, #5 dissecting forceps all in 70% EtOH

Frosted glass slides in 70% EtOH

One large watch glass (sterile) with cork stand

Several 100 mm Petri dishes

Ten 96-well culture dishes with feeder cells (prepared as indicated above)

SP 2/0 Myeloma cells (prepared as indicated above)

Water bath at 37° C.

1 ml PEG 1500 at 37° C. (Polyethylene Glycol, 2 gms in 75 mM

HEPES (N-2-hydroxyethylpiperazine-N-2 ethane sulphonic acid)

10 ml D-MEM/10% FBS/2× antibiotic 100 ml D-MEM (serum-free) on ice 25 ml D-MEM (serum-free) at 37° C.

Two 50 ml plastic centrifuge tubes (sterile)

Hemocytometer

Super HAT at 37° C.

Cell Freezing Medium at 37° C.

Method

1. Two frosted slides were removed from the EtOH and placed in a sterile Petri dish under a hood so that they would air-dry.

2. The mouse was sacrificed by cervical dislocation and immersed in 70% EtOH. After several minutes the mouse was placed on the large watch glass with its left side up.

3. A sterile 100 mm Petri dish with 5 ml D-MEM/10% FBS/2× antibiotic was set up for receiving the spleen.

4. The skin and then the abdominal wall were opened on the left upper quadrant of the mouse.

5. The spleen was removed and placed in the Petri dish. Using the dissecting forceps, as much of the white fibrous connective tissue as possible was removed. The cleaned spleen was placed into another Petri dish with D-MEM/10% FBS/2× antibiotic.

6. Any residual EtOH was flame dried from the glass slides. The slides were then used to slice the spleen into three pieces. Each of these pieces was then gently ground between the frosted ends of the slides to liberate the spleen cells. The cell suspension was then aspirated with a pipet, large pieces of connective tissue sank immediately to the tip. These were then discarded and the remaining cell suspension was transferred into a sterile 50 ml centrifuge tube.

7. Another 5 ml of the D-MEM/10% FBS/2× antibiotic was added to the Petri dish and this was used to collect residual cells. The solution was pipeted as above, the cells added into a 50 ml centrifuge tube, and placed on ice.

8. The SP 2/0 myeloma cells were collected by centrifugation in a sterile 50 ml centrifuge tube. At the same time, the spleen cells were pelleted at 1000 rpm for 5 minutes.

9. Both sets of cells were washed three times with 5 ml of cold, serum-free D-MEM (i.e. serum interferes with the fusion of these two cell types).

10. Both sets of cells were then resuspended in 5 ml of ice cold serum-free D-MEM by gently tapping and pipetting. These cell suspensions were kept cold on ice.

11. The spleen cells were then counted using the hemocytometer. A 30 $\mu$l aliquot of cells was taken and added to 30 $\mu$l of 4% acetic acid. The acid lysed the RBCs and made it easier to count the splenocytes. The sample was applied to the hemocytometer and the cells were counted in 25 large squares. This number, X, when divided by 50 gave the concentration of cells, in millions per ml. There was approximately 100 million spleen cells total. Only ten million spleen cells were used in the fusion. The rest were frozen. These cells were then thawed, washed twice with serum-free D-MEM, and used for another fusion. For this reason, the cells were frozen in aliquots of ten to twenty million cells per vial.

12. The fusion process was performed using a 3:1 ratio of spleen cells to SP 2/0 cells (i.e. the SP 2/0 cells were counted and approximately 3 million cells were used, this gave about 700–800 growing wells out of the 960 initially seeded). The SP 2/0 cell suspension was then added to the spleen cells and the mixture was spun for 5 minutes at 1000 rpm. All of the supernatant was removed thereby leaving the pellet as dry as possible. The pellet was loosened by tapping the tube briskly. It was important to break up this pellet so that the PEG would contact as many cells as possible.

13. The tube was then placed in a 37° C. water bath. PEG solution (the fusion promoter; 1 ml at 37° C.) was added drop wise directly onto the pellet over a full one minute-period. The tube was rotated while the PEG was added. To suspend the cells, the tube was gently swirled. The mixture was then allowed to sit in the water bath for about one minute.

14. While rotating the tube 1 ml of 37° C. serum-free DMEM was added over a one minute period.

15. Serum-free DMEM (20 ml at 37° C.) was then added over a four minute period.

16. At 1000 rpm the mixture was spun for five minutes. The supernatant was immediately removed and the pellet was resuspended in 100 ml Super HAT medium. An aliquot of this suspension (0.1 ml) was placed in each well of the ten plates containing the macrophages.

Feeding Schedule

The cultures were fed after fusion through the replacement of a portion of the culture medium with fresh medium. As a result, the feeding gradually diluted out any of the antibody made by normal (unfused) antibody-secreting spleen cells while also removing waste product and replenishing the nutrients.

1. After 3 days 0.1 ml of medium was removed from each well taking care not to disturb the cell layer and replaced with fresh Super HAT.

2. The medium was charged again at 5 days. Most of the cells (i.e. unfused spleen cells and unfused myeloma cells) were dead or dying at this stage. After a week in Super HAT medium, it was assumed that all of the parental myeloma or spleen cells were dead, and any growing cells were hybrids. The macrophages cleared much of the debris present in the medium. If the medium turned yellow and there were no colonies of hybridoma cells observed, the medium was charged again at 7 days. If the medium was yellow and there were colonies of growing cells observed, the medium was screened for the presence of antibody.

3. By 7 to 10 days after fusion, beautiful colonies of hybridoma cells were apparent. They were observed growing on the periphery of each well. Out of the 960 wells plated, 764 wells exhibited hybridomas.

4. The culture supernatant (50 $\mu$l) was then removed for screening when ¼ to ⅓ of each well was covered with growing cells.

III. Preliminary Screens Prior to Cloning

There were two general screening methods used to characterize the antibodies that were secreted by the various hybridomas: the Enzyme-Linked Immunosorbent Assay (or ELISA Assay) and the Indirect Immunofluorescence Assay. What follows is a summary of how these assays were used to screen the hybridoma colonies present in the 764 wells to identify those hybridomas which produce antibodies with the specificity for the cultured marrow mesenchymal stem cells.

A. IgG ELISA—When the colonies initially became visible the culture supernatant was screened by ELISA to goat anti-mouse IgG. This screen was set up to identify any colony composed of hybridomas which secrete antibodies with the IgG isotype. Since this isotype is the major secretory antibody and is also the easiest to purify and use, it was preferred and screened for instead of the IgM and IgA isotopes which may also contain specificity for the desired epitope.

Protocol for Goat anti-mouse IgG ELISA Assay
Preparation of goat anti-mouse IgG ELISA plates 1. 500 $\mu$l of goat anti-mouse IgG (Organon Teknika, Catalog #06110081) was diluted in 100 ml of Dulbecco' PBS (D-PBS) (GIBCO) and 50 $\mu$l were added to each well of 96 well vinyl microtitration plates (GIBCO).

2. Antibody was allowed to incubate for one hour at room temperature.

3. Plates were then rinsed twice with D-PBS containing 1% bovine serum albumin (BSA), and then incubated with D-PBS containing 1% BSA for one hour to block non-specific protein binding sites.

4. Plates were rinsed once with D-PBS containing 0.1% BSA, sealed in plastic bags and stored at 4° C. until use.

Running of ELISA Assay 1. 50 $\mu$l aliquots of antibody culture supernatants were added to wells on the ELISA plates and allowed to incubate in a humidified chamber for one hour at room temperature.

2. Plates were rinsed four times with Tris-buffered saline (TBS) containing 0.1% BSA.

3. Alkaline phosphatase-conjugated goat antibody specific for mouse IgG, IgM, and IgA (Organon Teknika, Catalog #86110231) was diluted 1:100–1:250 in TBS with 0.1% BSA and 50 $\mu$l was added to each well for one hour at room temperature in a humidified chamber.

4. Plates were rinsed four times with TBS with 0.1% BSA.

5. 0.0093 g of Phosphatase Substrate (Sigma) was dissolved in 10 ml of Substrate buffer which was composed of 50 mM glycine and 1 mM $MgCl_2$ pH 10.5. 50 $\mu$l was added to each well and allowed to incubate at 37° C. for one hour. A yellow color in the wells was interpreted as positive antibody reactivity.

6. Positive and negative controls consisted of identical analysis of immunized mouse serum and culture medium, respectively.

The results of the assays indicated that of the 764 wells which exhibited hybridoma growth, only 245 wells tested positive for the secretion of antibodies with the IgG isotype. This is demonstrated in the photograph of the ELISA assay results shown in FIG. 5.

B. Frozen Sections of Pelleted Cells by Indirect Immunofluorescence. Culture supernatant from colonies that were positive for IgG were then screened against frozen sections of pelleted cultured mesenchymal stem cells by indirect immunofluorescence. This assay was designed to identify antibodies which bonded to epitopes on the cultured marrow-derived mesenchymal cells.

Protocol of Antibody Binding to Pelleted Cultured Human Marrow Cells by Indirect Immunofluorescence Assay Preparation of Frozen Sections of Culture-expanded Human Mesenchymal Stem Cells 1. 4 ml of 0.25% Trypsin with 1 mM EDTA (GIBCO) was added to confluent cultures of human mesenchymal stem cells in 100 mm culture dishes and allowed to incubate at 37° C. for five minutes.

2. The enzymatic activity of the trypsin was stopped by addition of 2 ml of calf serum. The cells were pelleted by centrifugation at 1000×g, and the supernatant was discarded. The pelleted cells were rinsed two times with PBS.

3. After the second rinse the supernatant was removed and the cell pellet was dispersed into a small cup containing OCT Tissue Tek Compound (Miles Inc.) and frozen in liquid nitrogen. Frozen blocks of cells were stored at 0° C. in plastic bags until sectioned.

4. The blocks of tissue were sectioned at 6 microns/section and placed on gelatin coated slides. Slides were stored at 0° C. in slide boxes until needed.

Indirect immunofluorescent staining

1. Slides were removed from the freezer and allowed to warm to room temperature before using.

2. The sections were covered with 50–100 µl of antibody culture supernatant and incubated at room temperature for one hour in a humidified chamber. The slides were rinsed four times with 0.1% BSA-PBS.

3. The sections were then covered with 50 µl of FITC-conjugated Goat anti-mouse IgG (Organon Teknika, Catalog #1211-0231) which had been diluted 1:100 to 1:200 with 0.1% BSA-PBS and were allowed to incubate for one hour at room temperature in a humidified chamber.

4. The slides were rinsed four times with 0.1% BSA-PBS and coverslipped with a drop of PPD immunofluorescence mounting medium, and observed with an Olympus BH-2 epifluoresence microscope.

5. Negative control slides consisted of identical analysis of cells with culture medium which did not contain antibody.

The test results identified those antibodies which bonded to epitopes on the cultured mesenchymal stem cells. See FIGS. 6A–6H which are photomicrographs of typical frozen sections of pelleted culture-expanded human marrow derived cells. In addition, close observation of the staining pattern gave an indication of the cellular location of the antigen; intracellular, cell surface, or both. Of interest were only the antibodies which reacted to the cell surface, however since interpretation of the immunofluorescence pattern for intracellular or cell surface was not 100% accurate, all of the antibodies which react to any part of the cultured marrow cells were kept, and those antibodies which gave a negative response were screened out. Out of the 245 wells which tested positive for IgG secretion, 171 of these wells tested positive to frozen sections of pelleted cultured marrow cells.

C. Indirect Immunofluorescence to Live Cells in Micromass Cultures—Cultured human marrow-derived mesenchymal stem cells were replated into a small mass on the center of a tissue culture dish. This type of culture is referred to as a micromass. The cells normally remain viable, spread and replicate in these masses. Hybridoma supernatants which indicated positive reactivity to the screens as parts A and B were incubated with the cells in these micromass cultures and the reactivity was measured by indirect immunofluorescence according to the protocol set forth below. Since the cells being analyzed in this assay were living cells, this assay identified antibodies which bonded only to the cell surface of the cell and gave negative results to antibodies which bonded to intracellular epitopes.

Protocol of Antibody Binding to Living Culture-expanded Marrow-derived Cells in Micromass Preparation of the micromass cultures 1. Cells from confluent marrow-derived mesenchymal cell cultures were released with 0.25% trypsin containing 1 mM EDTA as described above. After stopping the activity of the trypsin with calf serum, the cells were pelleted by centrifugation and the supernatant was removed.

2. Cells were rinsed once with 5–10 ml $BGJ_b$ Complete medium and then were resuspended in Complete medium at a concentration of 500,000 cells per ml. 50 µl of cell suspension was transferred to the center of a 35 mm tissue culture dish (Falcon) and incubated overnight at 37° C.

Indirect immunofluorescent staining

1. The 35 mm dishes were rinsed three times with PBS. 100 µl of aliquots of antibody culture supernatants were added to each dish and incubated for one hour at room temperature in a humidified chamber.

2. Dishes were rinsed three times with 0.1% BSA-PBS, then 100 µl of FITC-conjugated Goat antibody specific for mouse IgG was added to each plate after being diluted 1:100 to 1:200 with 0.1% BSA-PBS. Dishes were incubated for one hour at room temperature in a humidified chamber.

3. Dishes were rinsed three times with 0.1% BSA-PBS and coverslipped after applying a drop of PPD immunofluorescent mounting medium. Immunofluorescent staining was observed using an Olympus BH-2 epi-fluoresence microscope.

Utilizing the above described protocol, out of the 171 wells which tested positive both for IgG secretion and the specificity to frozen pelleted cultured marrow cells, only 15 of these wells tested positive to specificity to living cultured marrow-derived mesenchymal stem cells. The photomicrographs in FIGS. 7A–7H illustrate the typical results of an indirect immunofluorescence analysis of living cultured marrow-derived mesenchymal stem cells in micromass.

IV. Cloning by Limited Dilution of Selected Colonies

The hybridomas which tested positive to each of the three preliminary screens (i.e. the 15 wells) were cloned by the following process in order to ensure that the subsequent screening steps were performed on hybridomas which originated from a single clone. Since multiple cell lines are usually present in the original "parent" well, cloning of the cells was required to obtain a monoclonal hybridoma cell line. By replating cells at a density of less than one cell per well, any colony which grew in a well should be the progeny from that cell. When all the growing wells contained the antibody of interest for two serial clonings, the cell line was considered to be monoclonal. In addition, the cloning by limited dilution was also performed in order to reduce the risk of overgrowth by non-producer cells.

Preparation of Feeder Layer Cells and Conditioned Medium

1. Mouse splenocytes were used instead of macrophages at this stage. Although the splenocytes were easier to collect, they added to the debris in the wells whereas the macrophages actually cleared the debris.

2. A mouse was sacrificed and its spleen was removed as described above.

3. The cells were liberated as previously described, counted, and added to 37° C. Super HAT so that their concentration was 1 million per ml.

4. When 96 well plates were used for plating, 0.1 ml of this suspension was added to each well. When 24 well plates were used for plating, 0.5 ml of this suspension was added to each well.

5. Alternatively, this cell suspension was also grown in large culture flasks (20 ml) for up to three days. During those three days, the suspension was used to create feeder layers. If the cells were not used within the three days, the medium was collected by passing the suspension through a sterile 0.22 μm filter. This medium, which can be stored at 4° C. for several weeks, was a useful additive for poorly growing cultures. However, this medium was not used instead of feeder layers.

Cloning

1. In all of the cases below, the cells were plated into wells already containing a feeder layer (see above).

2. The cells and medium were transferred from the selected parent wells of a 96-well plate to one well in a 24-well plate.

3. 200 μl of medium was added back to the parent wells so that residual parent cells could continue to grow. The parent wells served as back-ups in case of error.

4. Cell growth was monitored in the 24-well plate. It generally took about 3 to 7 days for a growing colony to cover half the well. In those wells which exhibited slow growth, additional conditioned medium was added.

5. When the cells were growing nicely, the medium was again screened for antibody. Since there was no point in cloning these cells if they had stopped secreting antibody, this was a necessary step.

6. If the antibody of interest was present, a small aliquot (50 μl) of cells was removed from the edge of the colony. This is normally where the most actively growing cells are found.

7. 10 μl of this aliquot was added to 30 μl of 0.5% Trypan blue dye. The viable cells were counted, the dead cells appeared blue. It was important to account for the dilution with Trypan when the final cell concentration was determined.

8. The remaining 40 μl aliquot was manipulated so that 100 cells were removed with certainty.

9. These 100 cells were added to 20 ml of Super HAT, the suspension was mixed and evenly plated into two 96-well plates. This resulted in two plates of cells at 0.5 cells per well.

10. Colonies developed in about half of the wells within 5 to 10 days. The fast growing colonies were screened for antibody. When positive colonies were found, four of the colonies were transferred to new wells on a 24-well plate.

11. 200 μl of medium was added back to the 96-well plate, and the new 24-well plate was treated exactly as the original 24-well plate above. This provided another source of back-up cells if cloning (or anything else) fails. Approximately 3 million cells were frozen per vial.

12. Approximately two weeks after the fusion, the cells were switched from Super HAT to Super H+T medium.

13. Cloning was continued using the above techniques until 100% of the subclones were positive for two generations.

14. The successively more "clonal" cells were also frozen for precautionary measures.

15. Once it was satisfied that the cell line was monoclonal, the culture medium was changed to Hybridoma 20%. This medium, which allows for enhanced cell growth, consisted of 78 ml D-MEM, 20 ml FBS, 1 ml Glutamine (Gibco #320-5030), 1 ml Solution I (See above), 0.1 ml Gentamicin (M.A. Bioproducts #17-5187).

V. Recovering the Monoclonal Antibodies Secreted by the Hybridomas

The monoclonal antibodies secreted by the cloned hybridomas were recovered by either culturing the cloned hybridomas (individually) in the hybridoma 20% medium and recovering the antibody from the medium or culturing the cloned hybridomas intraperitoneally in mice and harvesting the antibody containing the malignant ascites or serum from the mice. In this regard, through the use of the following procedure, hybridoma cells grown in the peritoneal cavity of the mice produced an ascitic fluid rich in monoclonal antibodies.

1. The recipient mouse was "primed" 5 to 10 days prior to tumor cell inoculation by intraperitoneally injecting each mouse with 0.5 ml of Pristane (2, 6, 10, 14, Tetramethylpentadecane; Sigma, Catalog #T-7640). The mice which were used to grow the tumors were of the same strain as that used to initially generate the hybridoma cell lines. The mice used were approximately 8 to 12 weeks of age. One tumor line was grown in 6 mice at a time.

2. In culture, the established monoclonal cell line was grown in log phase. Approximately 30 million cells were collected.

3. The cells were spun at 1000 rpm for five minutes and then removed from the culture supernatant.

4. Since the serum interferes with tumor production and contaminates ascites fluid, the cells were washed in serum-free medium and spun again.

5. The cells were resuspended in serum-free medium (i.e. DMEM-HG, Gibco, Grand Island, N.Y.) such that the final cell density was 10 million per ml.

6. Using a 23 gauge needle, 0.5 ml (5 million cells) of the suspension were injected into the peritoneum of each recipient mouse.

7. Approximately one week later, the mice appeared to have "bloated" abdominal cavities. Once they appeared to have enlarged to about the size of a plum, the ascites fluid present in the peritoneal cavity was tapped.

8. During tapping the mice were lightly anesthetized using Metafane (Methoxyflurane; Pitman-Moore, Inc., Catalog #NDC 11716-5943-4). Using a 22 gauge needle, the abdominal skin was pierced so that the needle was very superficially within the peritoneum. The ascites fluid then dripped out of the needle and into an awaiting vessel. By moving the mouse and/or the needle, it was possible to get as much as 5 mls of fluid. This fluid yielded antibody in the range of 0.5 to 5 mg/ml.

9. The animals were placed back in their cages for recovery and further tapping.

10. In the animals which did not recover from anesthesia at any stage of the experiment, the residual ascites fluid was obtained by surgically opening the abdomen and removing pooled fluid. In this regard, it was important that the fluid was not collected from mice which had been dead for more than one hour.

11. Once the fluid was collected, it was spun at 3000 rpm for 5 minutes to pellet out the RBCs and other undesirable cells.

12. Sodium azide was then added so that its final concentration was 0.02%. This ascitic fluid was then stored in small aliquots at −70° C. The stability of each antibody to freezing and thawing was tested before the entire ascites prep was frozen.

VI. Screening of Cloned Hybridomas

The cloned hybridomas (15 wells) were screened against a series of mesenchymal and non-mesenchymal derived tissues to identify the degree of specificity of the monoclonal antibodies to the cultured marrow-derived mesenchymal stem cells.

The test results of the three optimal hybridomas, i.e. SH2, SH3, and SH4 were evaluated against a control for background noise. The results are set forth below in Table 4. Along this line, in Table 4, (−) indicates no visible reactivity above the control; (±) indicates less than 1% reactivity above the control and for evaluation purposes was taken to be (−); and, (+) indicates substantial reactivity above the control. The negative control in each experiment involved incubating the cells or tissue of interest with SB-1, a monoclonal antibody to chicken alkaline phosphatase which does not react with human cells (without antibody), followed by rinsing the incubation with FITC-labelled second antibody.

A. The first level and most important level of specificity was that the monoclonal antibodies did not react to the hematopoietic lineage cells in marrow. To determine this, whole marrow and several partial fractionations of marrow were screened against hybridoma culture supernatant by indirect immunofluorescence according to the protocol set forth below. With fluorochrome isothiocyanate (FITC), the positive cells, and the percent positive cells, were noted, however, all hybridomas were kept for screening at the next level.

Preparation of Marrow

Whole marrow and low density Percoll fractions were prepared as described above in Example 1 and processed for frozen sections as described above for culture-expanded marrow-derived mesenchymal stem cells.

Indirect Immunofluorescence Staining

Sections of whole marrow and low density Percoll fractions were screened with antibody culture supernatant from cloned hybridomas using the same procedure as described above for screening culture expanded mesenchymal stem cells in frozen sections.

B. Screening of Monoclonal Antibodies Against Mesenchymal Derived Tissue—A variety of mesenchymal tissues were obtained at surgery or autopsy to determine if the monoclonal antibodies reacted to epitopes common to marrow-derived mesenchymal stem cells and differentiated mesenchymal tissues. Frozen sections of the tissues were screened against hybridoma culture supernatant and analyzed by indirect immunofluorescence according to the following procedure.

Detailed Protocol for Screening Tissue Section to Cloned Hybridoma Supernatants by Indirect Immunofluorescence Preparation of the tissue section 1. The following tissues were obtained as surgical biopsies or at autopsy from human patients: skin, foreskin, intestine, heart, skeletal muscle, lung, liver, brain, tendon, ligament, gall bladder, articular cartilage, femur, rib cartilage, and periosteum.

2. The following animal tissues were also obtained for screening: chicken bone and marrow, rabbit bone and marrow, rat bone, and bovine cartilage and bone.

3. The tissues were each embedded in OCT-Tissue Tek Freezing Medium (Miles Inc.) and frozen into blocks in liquid nitrogen and stored at 0° C. until use.

4. The tissue blocks were sectioned at 6 microns and placed on gelatine coated slides and stored at 0° C. until use.

Indirect Immunofluorescence Staining

Tissue sections were screened against hybridoma culture supernatant from cloned hybridomas using the same procedure as described above for screening culture-expanded cells in frozen sections.

The positive and negative reactivities were noted and the patterns of reactivity described (Table 4). All cloned hybridomas were kept for screening at the next level.

C. Screening of Monoclonal Antibodies Against Non—mesenchymal—derived Tissues—The overall objective of this screening protocol was to identify hybridomas which secreted antibodies which were specific for marrow-derived mesenchymal stem cells and/or their lineage descendants. An antibody which reacted to non-mesenchymal derived tissue was therefore not as specific or unique. Many non-mesenchymal derived tissues were obtained at autopsy and frozen sections were prepared. Hybridoma culture supernatant was incubated with these sections and antibody reactivity was analyzed by indirect immunofluorescence as described above. The positive and negative reactivity was identified as well as the pattern of reactivity.

TABLE 4

Reactivity of Optimal Hybridomas and Associated Monoclonal Antibodies with Various Tissue Cells

| | | Monoclonal Antibodies | | |
|---|---|---|---|---|
| | | SH2 | SH3 | SH4 |
| A. | Preliminary Screens | | | |
| 1. | IgG-ELISA | + | + | + |
| 2. | Pelleted Cultured Cells | + | + | + |
| 3. | Micromass of Cultured Cells | + | + | + |
| B. | Marrow Hematopoietic Cells | | | |
| 1. | Fresh Whole Marrow | − | ±[a] | ±[a] |
| 2. | Low Density Percoll Fraction | ±[a] | − | − |
| C. | Mesenchymal-Derived Tissues | | | |
| 1. | Femoral Head (bone) (HCl) | − | − | − |
| 2. | Rib bone and marrow (RDO) | ±[b] | − | − |
| 3. | Rib cartilage | − | + | − |
| 4. | Skeletal muscle | − | − | − |
| 5. | Cultured Periosteal Cells | − | + | + |
| 6. | Cultured Periosteal Cells (micromass) | − | + | + |
| 7. | Ligament | ±[b] | ±[b] | − |
| 8. | Tendon | − | − | ±[b] |
| 9. | Articular Cartilage | − | + | + |
| 10. | Femoral Shaft (RDO, HC1) | − | − | − |
| D. | Non-Mesenchymal Derived Tissues | | | |
| 1. | Foreskin | − | − | − |
| 2. | Breast skin | − | − | − |
| 3. | Intestines | ±[b] | − | − |
| 4. | Heart | ±[b] | − | − |
| 5. | Lung | ±[b] | − | − |
| 6. | Liver | ±[b] | ±[b] | − |
| 7. | Brain | − | − | − |
| 8. | Gall Bladder | − | − | + |

[a]Less than 1% over control
[b]Reactivity to tissue matrix not associated with cells The above results clearly indicate that three hybridomas, i. e. SH2, SH3, and SH4 have been identified and cloned. These hybridomas are useful for the analysis of marrow-derived mesenchymal stem cells. All three of the hybridomas secrete antibodies which react with the cell surface epitopes on 99–100% of cells in assays of culturally expanded marrow-derived mesenchymal stem cells. In contrast, each of the three hybridomas secrete antibodies which react with less than 1% of the cells in assays of whole marrow. The ability of these antibodies to selectively bind marrow-derived mesenchymal stem cells and not hematopoietic cells makes them excellent probes for quantitating the number of marrow-derived mesenchymal stem cells in samples of marrow as well as for purifying such cells from marrow.

In addition, all three of the hybridomas showed mostly negative cross-reactivity when screened against a variety of mesenchymal and non-mesenchymal derived tissues, although some cross reactivity was observed with each. Of particular interest, SH3 and SH4 cross-reacted to cell surface determinants on cultured cells derived from human periosteum. Since the inventors have previously shown periosteum to be another source of mesenchymal stem cells, the cross reactivity of the above antibodies to cell surface epitopes on periosteal cells suggests a structural relationship between the marrow-derived mesenchymal stem cells and periosteum-derived mesenchymal stem cells. When first tested the SH2 antibody, however, did not react to periosteum-derived mesenchymal stem cells even though it did bind to marrow-derived mesenchymal stem cells. This selectivity was thought to make the SH2 antibody useful for distinguishing between marrow-derived and periosteum-derived mesenchymal stem cells. It has since been observed that SH2 antibody does react with periosteum-derived mesenchymal stem cells also.

EXAMPLE 3

Antibody Differentiation of Mesenchymal and Hematopoietic Cells

The monoclonal antibodies produced above can also be utilized to distinguish between marrow-derived mesenchymal stem cells and marrow-derived hematopoietic cells. The ability to make such a distinction is useful for developing diagnostic reagents which quantitate the number of mesenchymal stem cells in samples of whole marrow. As a result, diagnostic reagents containing the monoclonal antibodies may then be used to identify patients with abnormally low mesenchymal stem cell numbers. A low level of mesenchymal stem cells may prove to be an indicator of abnormally low bone synthesis, which leads to osteoporosis.

In addition, monoclonal antibody-based diagnostic techniques are also useful for measuring the mesenchymal stem cell concentration in marrow harvested for future bone marrow transplantation. A low level of mesenchymal cells indicates a decreased probability of successful bone marrow transplantation because the marrow stroma will not develop quickly and completely without adequate mesenchymal stem cells to differentiate into stromal cells. In addition, assays which distinguish between marrow-derived mesenchymal cells and marrow-derived hematopoietic cells can also be used to purify mesenchymal stem cells from whole marrow. The purified cells may then be culture-expanded more efficiently and used to augment immune system reconstitution during bone marrow transplantation.

A procedure designed to demonstrate the effectiveness of the monoclonal antibodies, such as the SH2 mesenchymal stem cell monoclonal antibody produced above, to distinguish between marrow-derived mesenchymal stem cells and marrow hematopoietic cells would include the following processes:

(1) Indirect immunofluorescent staining to culture-expanded mesenchymal stem cells and whole marrow cells in suspension or solution.

(2) Indirect immunofluorescent staining of cryosections of culture-expanded mesenchymal stem cells and cryosections of whole marrow cells.

(3) Flow cytometric quantitation (or purification) of indirect immunofluorescent-stained culture-expanded mesenchymal stem cells mixed in a suspension of whole marrow cells.

EXAMPLE 4

Characterization of the Unique Human Mesenchymal Stem Cell Phenotype In Vitro

In a previous study, we reported on the isolation and culture-expansion of mesenchymal progenitor cells from human bone marrow with osteogenic and chondrogenic potential (Haynesworth, S. E. et al., Bone 13:81–88; 1992). We refer to these cells as Mesenchymal Stem Cells (MSCs). In culture, MSCs exhibit a fibroblastic morphology; however, identification of characteristic molecules is important for distinguishing MSC phenotype from its progeny such as lineage-committed and differentiated osteoblasts, chondrocytes and differentiated cells of the marrow stroma (stromocytes). A database of MSC phenotype markers also provides tools for assessing the effects of regulatory molecules on MSC differentiation. Such differentiation can be measured by the expression of these MSC stage-specific markers, relative to the onset of expression of molecules which are synthesized at distinct stages further along specific mesenchymal cell lineage pathways. We previously reported the identification of three MSC stage-specific molecules recognized by monoclonal antibodies that bind to cell surface eptiopes on MSCs in culture and in human marrow tissue, but not to most other human cells including osteoblasts, ostrocytes and chondrocytes (Haynesworth, S. E. et al., Bone 13:69–80; 1992). In the present study, we used immunological assays to probe for molecules synthesized and deposited by MSCs into the cell membrane and extracellular matrix (ECM), or secreted as soluble bioactive factors into the culture medium.

Isolation and culture-expansion of MSCs from human bone marrow was conducted in DMEM-LG supplemented with 10% fetal bovine serum (FBS) from selected lots (Control Medium) by our previously reported methods (Haynesworth, S. E. et al., Bone 13:81–88; 1992). Cell Surface and EMC Analysis: Cell surface and ECM antigens were probed through the use of commercially available antibodies and Stro-1 (Simmons et al., Blood 78:55–62 (1991) in indirect immunofluorescence assays on unfixed cultures of human MSCs replated onto 35-mm dishes in subconfluent monolayers or high density micromass cultures.

Cytokine Expression Analysis: Identification of selected cytokines synthesized and secreted by MSCs was conducted using quantitative ELISAs (R&D Systems) on subconfluent monolayer cultures of MSCs maintained in: Control Medium, or Control Medium "Osteogenic Supplements" (OS) (100 mM Dexamethasone, 10 mM β-glycerol phosphate and 50 μg/ml ascorbate); or "Stromogenic Supplements" (SS) (10 units/ml interleukin-1a (IL-1a)). OS cause MSCs to differentiate and express osteogenic characteristics including alkaline phosphatase and mineralized nodule formation (Bruder, S. P., et al., manuscript in preparation, 1994). SS has been reported to stimulate cytokine expression in marrow stromocytes (Bilips, L. G. et al., Blood 75(3):611–619, 1990). A list of the antigens found to be present or absent from the cell membrane and ECM of cultured human mesenchymal stem cells is summarized in Table 5.

TABLE 5

Cell Surface and EMC Expression Profile for Human MSCs

| Markers Present on the Cell Surface | Markers Absent from the Cell Surface | Markers Present in ECM | Markers Absent from ECM |
|---|---|---|---|
| CSPG, PDGFR, Integrins (α 1, 2, | Stro-1, von Wilebrand factor IGF-1R, bFGFR, Integrins (α4), | Collagens (I, III, V, VI, CSPG, Fibronectin | Collagens (II, IV, VII) KS Laminin, |

TABLE 5-continued

Cell Surface and EMC Expression Profile for Human MSCs

| Markers Present on the Cell Surface | Markers Absent from the Cell Surface | Markers Present in ECM | Markers Absent from ECM |
|---|---|---|---|
| 3, 5, and β 3, 4, 5) | CD (3, 10, 14, 15, 19, 25, 34, 44, 45) | | Elastin, BGP |

Epitopes to markers that identify differentiated mesenchymal phenotypes are not detected by our analysis including those synthesized by chondrocytes (type II collagen, keratin sulfate (KS)), osteoblasts (Bone Gia Protein (BGP)), basement membrane fibroblasts (laminin, elastin and type IV collagen), marrow stromal cell progenitors (Stro-1 antigen), and endothelial cells (von Wilebrand factor). In contrast: MSCs synthesize a unique set of surface and matrix proteins. Of particular interest are the set of collagens, where type VI collagen is the predominant collagen detected in human MSC cultures. This pattern of expression is clearly distinct from the patterns of collagen expression by osteoblasts or chondrocytes, and should prove useful in revealing developmental transitions along these lineage pathways.

MSCs also express a distinct profile of cytokines which is altered when they are exposed to OS or SS conditions. In Control Medium, MSCs express high levels of IL-6, but minimal or undetectable levels of several of the other cytokines tested. SS up-regulated the expression of G-CSF, GM-CSF, LIF, SCF, and IL-6. In contrast, OS down-regulates IL-6 expression but has no effect on the other cytokines assayed.

The cytokines assayed and their levels of secretion by MSCs after 3 days in the various culture conditions are shown in FIG. 8.

These data expand our understanding of the phenotypic characteristics of human MSCs in culture. The data show that MSCs display a set of macromolecules that is distinct from those associated with differentiated mesenchymal cell types including osteoblasts, chondrocytes, and marrow stromocytes. The data also show that as MSCs differentiate along mesenchymal lineage pathways (i.e., osteogenic or stromogenic) in response to local cues, new combinations and amounts of macromolecules are expressed. These observations advance the development of experimentation to unravel the mechanisms of control of MSC commitment and differentiation into phenotypically distinct cell types.

EXAMPLE 5

Cytokine Expression by Human Marrow-Derived Mesenchymal Stem Cells In Vitro: Effects of IL-1α and Dexamethasone The objective of the present study was to further establish the phenotypic characteristics of cultured MSCs through identification of a cytokine expression profile. We used commercial ELISAs to identify and measure the levels of expression of cytokines that are known to be important in the regulation of cell division, differentiation or expression of a variety of mesenchymal phenotypes. We identified MSC cytokine expression under culture conditions that we have previously reported allow MSCs to mitotically expand without differentiation (constitutive culture-expansion medium). In addition, we assayed cytokine expression by MSCs in culture medium supplemented with dexmethasone or IL-1α. Dexamethasone has been reported to induce the differentiation of osteo-progenitors into obstroblasts. In contrast, IL-1α, which is secreted into the marrow microenvironment by a variety of cells during the inflammatory response, has been reported to enhance the bone marrow stroma's capacity to support hematopoiesis and thus may play a role in controlling the differentiation and/or expression of bone marrow stromal fibroblasts.

The data from these analyses show that cultured MSCs express a unique cytokine profile. In addition, dexamethasone and IL-1α alter the MSC cytokine expression profile in different ways. These data add to our understanding of the unique phenotypic profile of MSCs, and also identify macromolecules whose expression is developmentally regulated as MSCs differentiate or modulate their phenotype towards the osteogenic lineage or marrow stromal phenotype.

MSC Isolation and Culture-Expansion

Bone marrow was obtained from six human donors, 3 male and 3 female of diverse ages (Table 6).

TABLE 6

Donor Characteristics

| Donor # | Donor Age | Clin. Cond. | Gender |
|---|---|---|---|
| 1 | 39 | NHL* | F |
| 2 | 58 | breast cancer | F |
| 3 | 38 | myelodysplasia | F |
| 4 | 3 | medulloblastoma | M |
| 5 | 28 | Hodgkin's Lymphoma | M |
| 6 | 47 | AML* | M |

*NHL = non-Hodgkin's lymphoma; AML = acute myelogenous leukemia

Each donor was in remission from cancer and was undergoing marrow harvested for future autologous bone marrow transplantation. Approximately 10 ml of unfractionated bone marrow was obtained from the harvest and used in the assays in this study. MSCs were purified and cultured by a modification of previously reported methods. Briefly, bone marrow aspirates were transferred from their syringes into 50 ml conical tubes containing 25 ml of complete medium consisting of Dulbecco's Modified Eagles Medium supplemented with fetal bovine serum (FBS) from selected lots, to a final volume of 10%. The tubes were spun in a Beckman table top centrifuge at 1200 rpm in a GS-6 swing bucket rotor for 5 min to pellet the cells. The layer of fat that forms at the top of the samples and the supernatants were aspirated using a serological pipet and discarded. The cell pellets were resuspended to a volume of 5 ml with Complete Medium and then transferred to the top of preformed gradients of 70% Percoll. The samples were loaded into a Sorvall GS-34 fixed angle rotor and centrifuged in a Sorvall High Speed Centrifuge at 460×g for 15 min. The low density fraction of approximately 15 ml (pooled density=1.03 g/ml) was collected from each gradient and transferred to 50 ml conical tubes to which were added 30 ml Complete Medium. The tubes were centrifuged at 1200 rpm to pellet the cells. The supernatants were discarded and the cells were resuspended in 20 ml of Complete Medium and counted with a hemocytometer after lysing red blood cells with 4% acetic acid. Cells were adjusted to a concentrated of $5 \times 10^7$ cells per 7 ml and seeded onto 100-mm culture plates at 7 ml per plate.

Culture and Passage of Marrow-derived MSCs

Marrow-derived MSCs were cultured in Complete Medium at 37° C. in a humidified atmosphere containing 95% air and 5% $CO_2$, with medium changes every 3–4 days. When primary culture dishes became near confluent, the cells were detached with 0.25% trypsin containing 1 mM EDTA (GIBCO) for 5 min at 37° C. The enzymatic activity of trypsin was stopped by adding ½ volume of FBS. The cells were counted, split 1:3, and replated in 7 ml of Complete Medium. These first passage cells were allowed to divide for 4–6 days until they became near confluent. Near-confluent first passage cells were trypsinized and replated into the assay formats as described below.

Quantitative ELISA

Levels of cytokine expression by MSCs were measured using quantitative ELISA. ELISA kits (R&D Systems, Minneapolis, Minn.) with antibody specificities for the following cytokines were purchased; interleukin-3 (IL-3), interleukin-6 (IL-6), interleukin-11 (IL-11), granulocyte colony stimulating factor (G-CSF), granulocyte-macrophage colony stimulating factor (GM-CSF), macrophage colony stimulating activity (M-CSF), stem cell factor (SCF), leukemia inhibitory factor (LIF) and transforming growth factor-beta-2 (TGF-$\beta$-2). Near-confluent, first passaged MSCs were replated into 35-mm plates at 50,000 cells per plate and allowed to attach overnight. Culture conditions were then changed to one of three test conditions: fresh Complete Medium; Complete Medium with osteogenic Supplement; and Complete Medium with Stromagenic Supplement. Cultures were allowed to incubate in test media for 24 or 48 hours at which points the supernatants were collected, flash frozen in dry ice-ethanol and stored at −70° C. in a Revco freezer until all of the samples were prepared to analyze together. Assays were conducted by applying 100 μl of culture supernatant onto the wells of the ELISA plate followed by processing the plates per manufacturer's instructions. Standard curves were generated using standard cytokines supplied with the kits and diluted to the appropriate concentrations. In some cases (particularly for the IL-6 assay), the supernatants had to be diluted substantially to generate low enough absorbance measurements that could be quantified accurately from the standard curves.

RESULTS

Constitutive Culture-Expansion Medium Condition

Detectable levels of six of the nine assayed cytokines were present after 24 hour exposure to constitutive culture-expansion conditions. See FIGS. 9A–9D and 10A–10C and see Tables 7–10 below).

TABLE 7

Detected Cytokine Levels (24 hours)

| Donor | G-CSF 24 h | GM-CSF 24 h | SCF 24 h | LIF 24 h |
|---|---|---|---|---|
| Control | 15 | 3 | 56 | 52 |
| 1 | | | | |
| 2 | 4 | 0 | 53 | 107 |
| 3 | 3 | 0 | 28 | 134 |
| 4 | 0 | 0 | 16 | 7 |
| 5 | 0 | 0 | 30 | 40 |
| 6 | 37 | 0 | 26 | 119 |
| Average | 10 | 1 | 35 | 66 |
| Std. Dev. | 14 | 1 | 16 | 51 |
| OS | 22 | 0 | 80 | 11 |
| 1 | | | | |
| 2 | 0 | 1 | 61 | 20 |
| 3 | 6 | 0 | 34 | 44 |
| 4 | 1 | 0 | 17 | 11 |
| 5 | 4 | 0 | 22 | 11 |
| 6 | 0 | 0 | 34 | 87 |
| Average | 6 | 0 | 41 | 31 |
| Std. Dev. | 8 | 0 | 24 | 30 |
| Pvalue con:OS | 0.5464 | 0.5761 | 0.1900 | 0.0274 |

TABLE 7-continued

Detected Cytokine Levels (24 hours)

| Donor | G-CSF 24 h | GM-CSF 24 h | SCF 24 h | LIF 24 h |
|---|---|---|---|---|
| Pvalue OS:SF | 0.0358 | 0.0054 | 0.4714 | 0.0176 |
| IL-1 | 322 | 527 | 66 | 644 |
| 1 | | | | |
| 2 | 966 | 741 | 83 | 622 |
| 3 | 1266 | 413 | 43 | 1008 |
| 4 | 143 | 198 | 28 | 152 |
| 5 | 410 | 307 | 0 | 191 |
| 6 | 164 | 210 | 69 | 338 |
| Average | 545 | 399 | 48 | 493 |
| Std. Dev. | 463 | 209 | 31 | 327 |
| Pvalue Con:SS | 0.038 | 0.0054 | 0.2434 | 0.0180 |

TABLE 8

Detected Cytokine Levels (24 hours)

| Donor | M-CSF 24 h | IL-11 24 h | IL-6 24 h | TGF-$\beta$ 24 h |
|---|---|---|---|---|
| Control | 200 | 830 | 7547 | 0 |
| 1 | | | | |
| 2 | 233 | 741 | 9887 | 0 |
| 3 | 303 | 659 | 6962 | 0 |
| 4 | 132 | 144 | 6987 | 0 |
| 5 | 130 | 509 | 5384 | 0 |
| 6 | 134 | 343 | 7761 | 0 |
| Average | 178 | 538 | 7421 | 0 |
| Std. Dev. | 70 | 259 | 1467 | 0 |
| OS | 548 | 0 | 1714 | 0 |
| 1 | | | | |
| 2 | 345 | 0 | 338 | 0 |
| 3 | 550 | 52 | 1842 | 0 |
| 4 | 73 | 0 | 650 | 0 |
| 5 | 162 | 9 | 1111 | 0 |
| 6 | 170 | 0 | 919 | 0 |
| Average | 308 | 9 | 1096 | 0 |
| Stan. Dev. | 206 | 21 | 591 | 0 |
| Pvalue con:OS | 0.1119 | 0.0038 | 0.0004 | |
| Pvalue OS:SS | 0.0123 | 0.0375 | 0.0065 | |
| SS | 1222 | 3583 | 216666 | 0 |
| 1 | | | | |
| 2 | 1355 | 4277 | 255555 | |
| 3 | 2099 | 7351 | 340540 | |
| 4 | 290 | 355 | 76033 | |
| 5 | 753 | 1189 | 109473 | |
| 6 | 589 | 1226 | 122666 | |
| Average | 1051 | 2997 | 186822 | |
| Std. Dev. | 648 | 2620 | 101604 | 0 |
| Pvalue Con:SS | 0.0149 | 0.0569 | 0.0074 | |

TABLE 9

Detected Cytokine Levels (48 hours)

| Donor | G-CSF 48 h | GM-CSF 48 h | SCF 48 h | LIF 48 h |
|---|---|---|---|---|
| Control | 2 | 0 | 112 | 92 |
| 1 | | | | |
| 2 | 0 | 0 | 129 | 123 |
| 3 | 0 | 0 | 41 | 142 |
| 4 | 0 | 0 | 67 | 45 |
| 5 | 0 | 0 | 27 | 28 |
| 6 | 5 | 2 | 38 | 74 |
| Average | 1 | 0 | 69 | 84 |
| Std. Dev. | 2 | 1 | 42 | 44 |
| OS | 1 | 7 | 0 | 98 | 43 |
| | 2 | 0 | 0 | 76 | 22 |
| | 3 | 2 | 0 | 29 | 26 |
| | 4 | 10 | 0 | 100 | 40 |

TABLE 9-continued

Detected Cytokine Levels (48 hours)

| Donor | | G-CSF 48 h | GM-CSF 48 h | SCF 48 h | LIF 48 h |
|---|---|---|---|---|---|
| | 5 | 2 | 0 | 29 | 0 |
| | 6 | 0 | 0 | 17 | 8 |
| Average | | 4 | 0 | 58 | 23 |
| Std. Dev. | | 4 | 0 | 38 | 17 |
| Pvalue con:OS | | 0.3053 | 0.3632 | 0.3901 | 0.0171 |
| Pvalue OS:SS | | P.0115 | 0.0027 | 0.1276 | 0.0040 |
| SS | 1 | 452 | 348 | 144 | 841 |
| | 2 | 989 | 564 | 162 | 795 |
| | 3 | 1214 | 291 | 53 | 866 |
| | 4 | 143 | 198 | 28 | 152 |
| | 5 | 410 | 307 | 0 | 191 |
| | 6 | 164 | 210 | 69 | 338 |
| Average | | 545 | 399 | 48 | 493 |
| Std. Dev. | | 463 | 209 | 31 | 327 |
| Pvalue Con:SS | | 0.038 | 0.0054 | 0.2434 | 0.0180 |

TABLE 10

Detected Cytokine Levels (48 hours)

| Donor | | M-CSF 48 h | IL-11 48 h | IT-6 46 h | TGF-β 48 h |
|---|---|---|---|---|---|
| Control | | 975 | 1414 | 11707 | 0 |
| | 1 | | | | |
| | 2 | 451 | 905 | 10598 | 0 |
| | 3 | 632 | 761 | 10691 | 0 |
| | 4 | 337 | 225 | 4878 | 0 |
| | 5 | 279 | 561 | 4814 | 0 |
| | 6 | 222 | 467 | 5645 | 0 |
| Average | | 483 | 722 | 8056 | 0 |
| Std. Dev. | | 282 | 413 | 3261 | 0 |
| OS | 1 | 867 | 184 | 1230 | 0 |
| | 2 | 530 | 0 | 493 | 0 |
| | 3 | 655 | 0 | 1395 | 0 |
| | 4 | 305 | 0 | 1090 | 0 |
| | 5 | 361 | 0 | 1134 | 0 |
| | 6 | 264 | 0 | 357 | 0 |
| Average | | 497 | 31 | 950 | 0 |
| Std. Dev. | | 233 | 75 | 422 | 0 |
| Pvalue con:OS | | 0.6513 | 0.0049 | 0.0029 | |
| Pvalue OS:SS | | 0.0114 | 0.0167 | 0.0152 | |
| SS | 1 | 1188 | 4735 | 182352 | 0 |
| | 2 | 1416 | 5500 | 36666 | 0 |
| | 3 | 1847 | 7351 | 349629 | 0 |
| | 4 | 290 | 355 | 76033 | 0 |
| | 5 | 753 | 1189 | 109473 | 0 |
| | 6 | 589 | 1226 | 122666 | 0 |
| Average | | 1051 | 2997 | 186822 | 0 |
| Std. Dev. | | 648 | 2620 | 101604 | 0 |
| Pvalue Con:SS | | 0.0149 | 0.0569 | 0.0074 | |

The cytokines expressed in terms of pg/10,000 cells in 24 or 48 hours, from lowest to highest were: G-CSF, SCF, LIF, M-CSF, IL-11 and IL-6. Three cytokines were not detected in the supernatants under constitutive culture-expansion conditions: GM-CSF, IL-3 and TGF-β2. Large differences were observed in the average cytokine expression of each cytokine in comparison to the average levels of expression of other cytokines. At the extremes, the average detectable level of G-CSF expression (10 pg/10,000 cells/24 hours) was over 700 fold lower than the average level of expression of IL-6 (7421 pg/10,000 cells/24 hours).

Osteogenic Supplement Culture Conditions

The addition of osteogenic supplements to complete Medium resulted in no detectable changes in G-CSF, M-CSF and SCF relative to control (FIGS. 9A–9D and 10A–10B; Tables 7–10). In contrast, OS medium significantly down-regulated the expression of LIF ($p<0.01$), IL-6 ($p<0.001$) and IL-11 ($p<0.005$) relative to the expression of these cytokines under constitutive culture-expansion medium conditions at 24 hours. These levels remained statistically lower than cytokine levels in constitutive culture-expansion medium conditions at 48 hours (FIGS. 9A–9D and 10A–10C; Tables 7–10). The amount of OS medium-mediated inhibition varied for the three cytokines; at the 24 hour timepoint the average level of cytokine expression in OS-medium relative to constitutive culture-expansion medium conditions was as follows; LIF expression 55%±54%, IL-6 16%±9% and IL-11 1%±3%. The large standard deviation in the LIF percent change was due primarily to the measurements from one donor (donor #4) where the level of LIF expression was actually higher under OS medium conditions relative to constitutive culture-expansion conditions (Table 7). For a given donor, the percent inhibition of a cytokine relative to the average absolute level of inhibition of that cytokine, was independent to the percent inhibition of the other two cytokines, relative to their average absolute levels of inhibition (Tables 7–10). In addition, for each of the cytokines, the percent inhibition for a given cytokine among the six individuals in the population, was independent of the initial levels of expression under constitutive culture-expansion conditions (FIGS. 9A–9D and 10A–10C; Tables 7–10).

Stromagenic Supplement Culture Conditions

SS medium increased the expression of several cytokines by MSCs in a concentration dependent manner. FIG. 11 illustrates the 24 hour response of second passage MSCs to increasing concentrations of IL-1α in terms of expression of GM-CSF. There is a near linear increase in the level of GM-CSF secretion by MSCs, with increasing levels of IL-1α in the culture medium between 0.1–10.0 U/ml. Additional log increases in IL-1α to the culture medium results in little additional increase in GM-CSF expression. These data were used to identify the concentration of IL-1α to supplement to the culture media in the experiments described below. For all subsequent assays, 10 U/ml IL-1α were added to the culture media.

Culture medium supplemented with 10 U/ml IL-1α induced statistically significant up-regulation in the expression of G-CSF ($P<0.05$), M-CSF ($p<0.02$), LIF ($p<0.02$), IL-6 ($p<0.01$) and IL-11 ($p<0.06$) relative to cells cultured in constitutive culture-expansion medium. In addition, IL-1α induced the expression of GM-CSF which was not detectable in constitutive culture-expansion medium. In contrast, IL-1α had no statistically significant effect on the expression of SCF relative to the level of expression under constitutive culture-expansion medium conditions. The fold increase in response to IL-1α varied depending on the cytokine. IL-6 (25.1±13.4 fold increase) was stimulated to the greatest extent, followed by LIF (9.2±6.9 fold), M-CSF (5.2±1.7 fold) and IL-11 (4.9±3.3 fold). The average fold increase for G-CSF and GM-CSF were not calculated, since these cytokines were not detected in some or all constitutive culture-expansion cultures.

DISCUSSION

Our continued analyses of MSCs in this study were aimed at identifying additional phenotypic characteristics, and determining how this phenotype is altered when MSCs are exposed to regulatory molecules that cause differentiation or phenotypic modulation. In this study, we used ELISA assays to characterize the cytokine expression of MSCs under constitutive culture-expansion conditions, and in the presence of OS or SS.

MSCs express a unique profile of cytokines which include G-CSF, M-CSF, SCF, LIF, IL-6 and IL-11 under constitutive culture-expansion conditions. They do not express GM-CSF, IL-3 and TGF-β under these conditions. OS down-regulates the expression of LIF, IL-6 and IL-11, while not affecting the expression of the other cytokines expressed under constitutive culture conditions. OS was not observed to up-regulate the expression of any of the cytokines assayed in this study. In contrast, SS up-regulates the expression of G-CSF, M-CSF, LIF, IL-6 and IL-11, and induces the expression of GM-CSF which was not detected under constitutive culture-expansion conditions. SS had no effect on SCF expression, and was not observed to down-regulate any of the cytokines assayed in this study. Through these data, a unique cytokine expression profile has been generated that can aid in identifying MSCs from other mesenchymal phenotypes. The identity of the cytokine profile should provide clues to determine the role that these cells play in the microenvironment of bone marrow which provides the inductive and regulatory information that supports hematopoiesis. In addition, the alterations in this cytokine profile in response to OS and SS, identify specific cytokines whose levels of expression change as MSCs differentiate or modulate their phenotype in response to regulatory molecules.

IL-1α, which is released in the marrow microenvironment by a variety of cell types during inflammatory responses, induces MSCs to up-regulate expression of cytokines that support granulocytic (G-CSF and GM-CSF), monocytic/osteoclastic (GM-CSF, LIF, M-CSF, IL-6) and megakaryocytic (IL-11) differentiation. IL-1α has been shown to protect bone marrow from radio- and hemo-ablation. The IL-1α-induced up-regulation of cytokine expression by MSCs likely plays a role in the mechanisms of IL-1α's protective effects.

Dexamethasone, which induces MSCs to differentiate into osteoblasts, attenuates the expression of monocytic/osteoclastic (LIF, IL-6) and megakaryocytic (IL-11) supportive cytokines, and has no effect on the expression of cytokines that support granulocytic progenitors (G-CSF, GM-CSF). The three cytokines inhibited by dexamethasone are of interest because each mediates its signal through a receptor that uses gp130 in its signaling pathway.

EXAMPLE 6

Preparation and Use of an MSC Enriched Extract

Bone marrow is harvested from the posterior iliac crest of a human patient under sterile working conditions. Bone marrow is aspirated from several sites from the sternum, rib and iliac crest. Aspiration is slow to avoid clotting in the syringe. Multiple aspiration sites from the bone with one or two skin penetration sites provides high nucleated cell counts contaminated with relatively low volume of diluting peripheral blood. The syringe is equipped with a conventional sternal aspiration needle, 12 gauge bone marrow aspiration trocar needle or trephine needle used for bone marrow harvesting. Twenty-five ml. of bone marrow is harvested into heparinized syringes 91000 units/liter of sterile saline).

The human bone marrow is then transferred to a 50 ml. centrifuge tube and centrifuged at low speed to yield a cell pellet. Fat and plasma are removed from the centrifuge tube by aspiration. The cell pellet is resuspended in a sterile solution containing 20 mM Tris base and 0.7% ammonium chloride. The cell pellet is then resuspended in the Tris NH$_4$Cl solution and the pH is adjusted to 7.2 and then centrifuged at low speed to yield a cell pellet. The Tris NH$_4$Cl solution is aspirated from the cell pellet and the pellet resuspended in 10 ml of DMEM medium. The resuspended pellet is carefully layered onto a 50 ml tube containing 35 ml. of 70% Percoll™. The tube is centrifuged at 460×g for 15 minutes. The upper 25% of the gradient or 12.5 ml of the Percoll gradient containing mesenchymal stem cells, platelets and other cells is harvested with a pipet. This fraction is transferred to a 50 ml centrifuge tube to which 25 ml of medium has been added. The tube is inverted several times to suspend the cells and then recentrifuged at low speed to yield a cell pellet. This process is repeated twice with fresh medium.

The human bone marrow sample is then concentrated to remove plasma and cleared of red blood cells either by NH$_4$Cl treatment as described above or by passage of the samples over a Leukosorb™ filter contained in a syringe cartridge filter removing fat, red blood cells and plasma. The cell fraction retained by the filter is eluted from the filter using a buffer containing sodium citrate. The MSC enriched cells which elute from the filter are then further enriched by passage over an hydroxyapatite column which preferentially binds MSCs. The syringe filter eluate containing red blood cell depleted bone marrow is passed over a syringe filled with hydroxyapatite. The hydroxyapatite used in this example is obtained from Interpore Corp. (IP200). Porous hydroxyapatite granules having a minimum pore size of 200 micrometers and a maximum pore size of up to 500 micrometers are used. The cells are loaded into the syringe containing hydroxyapatite in a sterile transfer step. The cells are allowed to bind for 15 minutes and buffer present in the cells allowed to flow through. The syringe is then washed one time with 15 ml. of medium (DMEM). The base of the syringe which is threaded is unscrewed and the implant material pushed out of the syringe with the piston for further processing or for direct intraoperative application to a graft site.

A monoclonal antibody separation is then performed as follows. Dynabeads M-450 (Dynal (r) Inc. Lake Success, N.Y.) are coupled to HB 10743, HB 10744 and HB 10745 antibodies by incubating 2.0 micrograms of the monoclonals per milligram of secondary coated Dynabeads in PBS. The bead solution containing 1×10$^7$ dynabeads per ml. is used. Antibody is incubated for 30 minutes with the beads at 4° C. The dynabeads are collected by placing the sample containing beads and monoclonal antibodies into the Magnetic Particle Concentrator. The supernatant is removed while the Dynabeads are kept on the wall of the test tube with the magnet. Dynabeads are cleared of free antibody by washing 5 times with PBS. After the last wash, the Dynabeads are collected and the supernatant is removed. To the 80 ml. of Dynabeads is added 35 ml. of heparinized bone marrow. The cells are incubated with the dynabeads for 15 minutes with shaking. The Dynabeads with attached MSCs are then collected using the Dynal MPC (Magnetic Particle Concentrator). The supernatant is removed and the magnetic particles washed concentration with PBS. Approximately 200×10$^6$ cells are collected on the Dynabeads. The cells are detached from the beads by incubating beads in 50 ml. of a solution containing 1% EDTA. The EDTA solution is removed from the cells by centrifugation at low speed. The cell pellet obtained may be resuspended in fibrinogen solution. Thrombin is added to the fibrinogen solution to establish clotting and form an implant.

Cells isolated as described above are resuspended at a concentration of 5.0×10$^6$ cells/ml. in serum free Ham's F-12. As a control, unfractionated whole bone marrow is centrifuged to yield a cell pellet and subsequently resuspended in Ham's F-12 to yield 5.0×10$^6$ cell/ml. Cells from each group are combined with ceramics in a 5 ml. Falcon tube, capped and infiltrated with cells by withdrawing a 5 ml. volume of air from the tube with a 10 ml. syringe fitted with an 18 gauge needle. The samples are then placed in a 37° C. incubator for 30 minutes prior to implantation. The ceramics are implanted into pockets formed on the back of the mouse by blunt dissection.

EXAMPLE 7

A. Cellular Repair of Skeletal Defects

Culturally expanded mesenchymal stem or progenitor cells may also be used to repair skeletal defects which normally do not heal. One class of skeletal defects that can be repaired, is the class of large skeletal defects in bone caused by injury or produced by the removal of large sections of bone infected with tumor. Under normal circumstances, this type of defect does not heal and creates nonunion of the bone. This type of defect can be treated by implanting cultured mesenchymal stem or progenitor cells contained in calcium phosphate ceramic vehicles into the defect site. The ceramic becomes osteoconductive to surrounding bone, thereby promoting bony ingrowth along the edges of the ceramic, which also result in stabilization of the implant in the defect. In addition, the mesenchymal stem or progenitor cells differentiate into osteoblasts, which then synthesize bone in the ceramic pores. After the cultured cells fill about one third of the pores of the ceramic with bone, the host cells brought in by the vasculature continue to make bone in the ceramics. Other host cells brought in by the vasculature then begin to remodel the newly synthesized bone and the ceramic vehicle. Eventually, the defect becomes filled with live bone with a marrow cavity in the middle, with the ceramic vehicle becoming completely degraded over time.

A second class of defect that can be repaired by the culture-expanded mesenchymal stem or progenitor cells of the present invention, is the damaged articular cartilage generated by trauma or by diseases such as osteoarthritis and rheumatoid arthritis. Under normal circumstances, damage to articular cartilage does not heal, except in very young individuals where the underlying bone is also damaged so that a bloody wound is created. This type of defect can be treated by implanting cultured mesenchymal stem or progenitor cells into the defect. The cells are formatted in carriers which hold the cells in the defect, and present them in a manner (round cell morphology) such that they differentiate into chondrocytes. In this regard, a suitable carrier is constructed of collagen or fibrin, since both have low antigenicity, are pliable to mold to the shape of the defect, and promote round cell shape (which applicants know to be important to induction of chondrocyte differentiation).

B. Anchoring Prosthetic Devices

The culturally-expanded mesenchymal stem or progenitor cells are also used to improve the anchoring of prosthetic devices used to replace badly damaged joints including the hip, knee, shoulder, elbow and hand. The established method for anchoring these devices is by the use of polymethyl methacrylate cement. Although fairly successful, this method results in a failure rate of about 5–10% due to cement cracking. A second, more recent method of anchoring prosthetic devices, is by the use of spaghetti wire which provides a surface for the ingrowth of osteogenic cells. The present invention can be used in conjunction with the spaghetti wire method thereby speeding the process of bony ingrowth. This is accomplished by coating the prosthetic device surfaces with whole marrow or cultured cells prior to implantation. These cells can also be pretreated with growth factors or cytokines to increase the rate and the amount of bone formation into the implant. Faster and more complete bony ingrowth results in stronger, longer lasting implants.

C. Augmentation of Marrow Transplantation

Marrow transplantation has become an increasingly popular treatment for patients with a variety of cancers. Treatment normally begins with the harvesting of marrow from patients during the period of remission. The harvested marrow is cryopreserved and stored until the patient becomes symptomatic, at which time the patient is treated with radiation and chemotherapy and then given back his/her own marrow to reestablish the marrow tissue destroyed during the radiation and chemotherapy treatment. This method is suboptimal because the stroma of the marrow, which is made from mesenchymal cells, is also destroyed by radiation and chemotherapy and is not reestablished prior to transplantation of the marrow hemopoietic cells. Furthermore, intact stroma has previously been shown to be necessary for hemopoietic stem cell differentiation.

An additional embodiment of the invention concerns the use of culture-expanded mesenchymal stem or progenitor cells to optimize the marrow transplantation process. At the time of marrow harvest, an aliquot is taken and introduced into culture. The mesenchymal stem or progenitor cells are isolated, purified and culturally expanded and then cryopreserved until the time of transplantation. The culturally-expanded cells are then injected into the patient prior to the reintroduction of the whole marrow in order to reestablish the marrow stroma and therefore speed the rate of hemopoiesis. Alternatively, the culturally expanded cells can be added to whole marrow prior to infusion of the whole marrow, to insure the whole marrow contains a sufficient quanta of mesenchymal stem or progenitor cells for rapid fabrication of the marrow stroma.

D. Stimulation of Remopoietic Cell Reservoir

From the procedures described in detail above, implantation of cultured mesenchymal stem or progenitor cells in ceramic blocks results in bone formation inside the pores of the ceramic, followed by establishment of a marrow cavity inside the newly layed bone. The cells that generate the marrow cavity must be supplied by the vasculature of the host, which quickly invades the pores of ceramic blocks within a few hours of being implanted. It is not clearly understood why composite grafts of culture mesenchymal cells and ceramics induce recruitment of hemopoietic stem cells and other marrow elements, however, the fact that this does occur allows for the use of these grafts as a way to sequester hemopoietic stem cells and generate a hemopoietic stem cell reservoir. The reservoir of hemopoietic stem cells can then be used in clinical applications such as marrow transplantation as an alternative method for harvesting hemopoietic stem cells.

EXAMPLE 7

Phase I Clinical Trial

Ex vivo Expansion & Subsequent Infusion of Human MSCs

In a phase I study applicants determined the feasibility of collection, ex vivo culture-expansion, and intravenous (IV) infusion of human MSCs. Patients (N=23) with hematologic malignancies in complete remission were enrolled. Ten ml bone marrow (BM) samples were obtained from the iliac crests, the mononuclear cells were separated (70% Percoll gradient), and adherent cells were culture-expanded for 4–6 weeks under conditions optimal for mitotic expansion of MSCs. Autologous MSCs were reinfused IV over 15 minutes. Diagnostic BM exam was repeated 2 weeks later for histologic assessment and in vitro hematopoietic progenitor cell cultures. Patients ranged in age from 18–68 (median:

44) years. Twelve patients previously had undergone an autologous (N=11) or syngeneic (N=1) BM transplant a median of 12 (range: 4–52) months prior to collection of MSCs. A median of 364×10$^6$ nucleated bone marrow cells (range: 103 to 1004×10$^6$) were used for ex vivo expansion of MSCs. Median # MSCs obtained after culture-expansion was 59.0 (range: 1.1 to 347)×10$^6$. Fifteen patients completed the ex vivo expansion and underwent MSC infusion. Median time to MSC infusion after collection was 37 days, and ranged from 28 to 49 days. Five patients in each of 3 groups were given 1, 10, and 50×10$^6$ MSCs. No adverse reactions were observed with the infusion of the MSCs. No patients on repeat diagnostic BM exam showed a significant change in BM cellularity (>20%) nor increase in hematopoietic progenitor colonies.

In summary, MSCs obtained from cancer patients can be collected, expanded ex vivo, and infused IV without toxicity. These cells have the potential to enhance the BM microenvironment and future trials will address their ability to enhance recovery of blood counts when given in conjunction with autologous peripheral blood progenitor cell transplantation.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of producing a connective tissue which comprises producing connective tissue in an individual in need thereof by administering to said individual a cell preparation containing human mesenchymal stem cells which is recovered from human bone marrow and which is substantially free of blood cells.

2. The method of claim 1 wherein the step of administering the cell preparation comprises applying said cell preparation to an area of a connective tissue defect.

3. The method of claim 1 wherein the mesenchymal stem cells are recovered from the individual being treated.

4. The method of claim 2 which further comprises administering a factor which stimulates differentiation of the mesenchymal stem cells into the type of connective tissue necessary for repair of said defect.

5. The method of claim 1 wherein the mesenchymal stem cells have been culture-expanded.

6. The method of claim 2 wherein the defect is a bone defect.

7. The method of claim 2 wherein the defect is a cartilage defect.

8. The method of claim 1 wherein the cell preparation is administered with a factor which induces differentiation of the human mesenchymal stem cells into said connective tissue.

9. The method of claim 1 wherein the tissue is skeletal tissue.

10. The method of claim 1 wherein the mesenchymal stem cells are essentially homogeneous.

11. The method of claim 2 wherein the cell preparation is administered in conjunction with a carrier.

12. The method of claim 1 wherein the connective tissue is stroma.

13. A method for producing a connective tissue comprising producing connective tissue in an individual in need thereof by administering to said individual an isolated cell preparation which has been enriched in human mesenchymal stem cells.

14. The method of claim 13 wherein the step of administering the cell preparation comprises applying said cell preparation to an area of a connective tissue defect.

15. The method of claim 13 wherein the mesenchymal stem cells are recovered from the individual being treated.

16. The method of claim 14 which further comprises administering a factor which stimulates differentiation of the mesenchymal stem cells into the type of connective tissue necessary for repair of said defect.

17. The method of claim 13 wherein the mesenchymal stem cells have been culture-expanded.

18. The method of claim 14 wherein the defect is a bone defect.

19. The method of claim 14 wherein the defect is a cartilage defect.

20. The method of claim 13 wherein the cell preparation is administered with a factor which induces differentiation of the human mesenchymal stem cells into said connective tissue.

21. The method of claim 13 wherein the mesenchymal stem cells are essentially homogeneous.

22. The method of claim 13 wherein the connective tissue is stroma.

23. The method of claim 1 wherein the connective tissue is selected from the group consisting of bone, cartilage, ligament, tendon and muscle.

24. A method for enhancing the implantation of a prosthetic device in connective tissue comprising the step of implanting a prosthetic device having human mesenchymal stem cells adhered thereto under conditions suitable for differentiating the cells into connective tissue.

25. The method of claim 24 wherein the conditions are suitable for differentiating the cells into skeletal tissue.

26. The method of claim 25 wherein the mesenchymal stem cells are in a cell preparation which is recovered from human bone marrow and which is substantially free of blood cells.

27. The method of claim 26 wherein the mesenchymal progenitor cells have been culture-expanded.

* * * * *